US012533502B2

(12) United States Patent
Venskytis et al.

(10) Patent No.: US 12,533,502 B2
(45) Date of Patent: Jan. 27, 2026

(54) INSTRUMENT SEAL

(71) Applicant: Intuitive Surgical Operations, Inc., Sunnyvale, CA (US)

(72) Inventors: Nathan A. Venskytis, Hamden, CT (US); Douglas S. Langley, Millford, CT (US); Jake A. Luckman, New Haven, CT (US); Stephen C. Chai, Fremont, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 792 days.

(21) Appl. No.: 17/055,113

(22) PCT Filed: May 8, 2019

(86) PCT No.: PCT/US2019/031393
§ 371 (c)(1),
(2) Date: Nov. 12, 2020

(87) PCT Pub. No.: WO2019/222004
PCT Pub. Date: Nov. 21, 2019

(65) Prior Publication Data
US 2021/0213269 A1 Jul. 15, 2021

Related U.S. Application Data

(60) Provisional application No. 62/671,862, filed on May 15, 2018.

(51) Int. Cl.
*A61M 39/06* (2006.01)

(52) U.S. Cl.
CPC ..... *A61M 39/06* (2013.01); *A61M 2039/0626* (2013.01); *A61M 2039/064* (2013.01);
(Continued)

(58) Field of Classification Search
CPC .......... A61M 39/06; A61M 2039/0626; A61M 2039/064; A61M 2039/0673;
(Continued)

(56) References Cited

U.S. PATENT DOCUMENTS 5,209,737 A 5/1993 Ritchart et al.
5,300,036 A 4/1994 Mueller et al.
(Continued)

FOREIGN PATENT DOCUMENTS

CN 1795831 A 7/2006
EP 2010072 A1 1/2009
(Continued)

OTHER PUBLICATIONS

International Preliminary Report on Patentability for Application No. PCT/US2019/031393, mailed on Nov. 26, 2020, 10 pages.
(Continued)

*Primary Examiner* — Kevin C Sirmons
*Assistant Examiner* — William R Frehe
(74) *Attorney, Agent, or Firm* — Schwegman, Lundberg & Woessner, P.A.

(57) ABSTRACT

A medical device may include a septum seal including a septum wall having portions defining a septum opening, and a plurality of flaps extending over the septum seal toward the septum opening, wherein the flaps define a flap opening that overlaps with the septum opening.

18 Claims, 19 Drawing Sheets

(52) U.S. Cl.
CPC ............... *A61M 2039/0673* (2013.01); *A61M 2039/0686* (2013.01)

(58) Field of Classification Search
CPC ... A61M 2039/0686; A61B 2017/0084; A61B 2017/3464; A61B 17/3462; A61B 34/30; A61B 50/00; A61B 34/35; A61B 90/00; A61B 2050/005; A61B 2050/0066; A61B 2050/0067
See application file for complete search history.

(56) References Cited

U.S. PATENT DOCUMENTS

| | | | | |
|---|---|---|---|---|
| 5,308,336 | A | 5/1994 | Hart et al. | |
| 5,342,315 | A | 8/1994 | Rowe et al. | |
| 5,385,552 | A | 1/1995 | Haber et al. | |
| 5,385,553 | A | 1/1995 | Hart et al. | |
| 5,407,433 | A | 4/1995 | Loomas | |
| 5,411,483 | A | 5/1995 | Loomas et al. | |
| 5,603,702 | A | 2/1997 | Smith et al. | |
| 5,628,732 | A | 5/1997 | Antoon, Jr. et al. | |
| 5,792,113 | A | 8/1998 | Kramer et al. | |
| 5,895,377 | A | 4/1999 | Smith et al. | |
| 5,989,224 | A | 11/1999 | Exline et al. | |
| 6,083,203 | A | 7/2000 | Yoon | |
| 6,258,065 | B1 | 7/2001 | Dennis et al. | |
| 6,482,181 | B1 | 11/2002 | Racenet et al. | |
| 6,551,282 | B1 | 4/2003 | Exline et al. | |
| 6,702,787 | B2 | 3/2004 | Racenet et al. | |
| 7,011,314 | B2 | 3/2006 | McFarlane | |
| 7,390,317 | B2 | 6/2008 | Taylor et al. | |
| 7,438,702 | B2 | 10/2008 | Hart et al. | |
| 7,470,255 | B2 | 12/2008 | Stearns et al. | |
| 7,481,795 | B2 | 1/2009 | Thompson et al. | |
| 7,837,612 | B2 | 11/2010 | Gill et al. | |
| 7,931,623 | B2 * | 4/2011 | Wing | A61B 17/34 604/167.05 |
| 7,981,092 | B2 * | 7/2011 | Duke | A61B 17/3462 604/264 |
| 8,007,471 | B2 | 8/2011 | Sauer et al. | |
| 8,029,475 | B2 * | 10/2011 | Franer | A61B 17/3462 604/167.01 |
| 8,137,266 | B2 | 3/2012 | Judson et al. | |
| 8,137,318 | B2 | 3/2012 | Schweitzer et al. | |
| 8,147,457 | B2 | 4/2012 | Michael et al. | |
| 8,485,970 | B2 | 7/2013 | Widenhouse et al. | |
| 8,636,686 | B2 | 1/2014 | Minnelli et al. | |
| 8,821,445 | B2 | 9/2014 | McFarlane | |
| 2004/0230161 | A1 | 11/2004 | Zeiner | |
| 2005/0077689 | A1 | 4/2005 | Hueil | |
| 2007/0255218 | A1 | 11/2007 | Franer | |
| 2008/0300545 | A1 | 12/2008 | Hsieh | |
| 2009/0105635 | A1 * | 4/2009 | Bettuchi | A61M 39/0693 604/167.03 |
| 2010/0016799 | A1 * | 1/2010 | Schweitzer | A61B 17/3462 604/167.01 |
| 2010/0261975 | A1 | 10/2010 | Huey et al. | |
| 2014/0018631 | A1 | 1/2014 | Kleyman | |
| 2015/0123355 | A1 | 5/2015 | Castro et al. | |
| 2015/0223833 | A1 | 8/2015 | Coffeen et al. | |
| 2017/0079637 | A1 | 3/2017 | Ortiz et al. | |
| 2018/0085145 | A1 | 3/2018 | Okoniewski et al. | |
| 2018/0104423 | A1 | 4/2018 | Minnelli et al. | |
| 2019/0059938 | A1 | 2/2019 | Holsten | |
| 2019/0059944 | A1 | 2/2019 | Holsten | |

FOREIGN PATENT DOCUMENTS

| | | | |
|---|---|---|---|
| JP | 2000501978 | A | 2/2000 |
| JP | 2005111263 | A | 4/2005 |
| JP | 2009119249 | A | 6/2009 |
| JP | 2010240436 | A | 10/2010 |
| WO | WO-2007121425 | A1 | 10/2007 |
| WO | WO-2015142794 | A1 | 9/2015 |
| WO | WO-2016186905 | A1 | 11/2016 |

OTHER PUBLICATIONS

International Search Report and Written Opinion for Application No. PCT/US2019/031393, mailed on Aug. 12, 2019, 17 pages (ISRG11240/PCT).
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP19804398.6, mailed on Nov. 23, 2021, 9 pages.
Partial European Search Report for Application No. EP24160334.9, mailed on Apr. 16, 2023, 14 pages.
Extended European Search Report for Application No. EP24160334.9, mailed on Aug. 20, 2024, 14 pages.

* cited by examiner

INSTRUMENT SEAL

CLAIM OF PRIORITY

This application is a U.S. National Stage Filing under 35 U.S.C. 371 from International Application No. PCT/US2019/031393, filed on May 8, 2019, and published as WO 2019/222004 A1 on Nov. 21, 2019, which claims the benefit of priority to U.S. Patent Application No. 62/671,862, filed on May 15, 2018, each of which is incorporated by reference herein in its entirety.

TECHNICAL FIELD

This document relates generally to medical devices, and more particularly, to instrument seals for creating a seal against a surgical instrument during a surgical procedure.

BACKGROUND

In a surgical procedure it may be necessary to create a seal between a surgical instrument. Maintaining such a seal may, for example, allow for creation of a pressure (e.g., insufflation pressure) in a patient, which may facilitate the surgical procedure or benefit the patient.

SUMMARY

An example medical device seal ("Example 1") may include a septum seal including a septum wall having portions defining a septum opening, and a plurality of flaps extending over the septum seal toward the septum opening, wherein the flaps define a flap opening that overlaps with the septum opening.

In Example 2, the medical device of Example 1 may be configured such that the septum seal includes a bellows portion extending around the septum wall.

In Example 3, the medical device of Example 1 or 2 may further include a slit seal comprising a slit portion and a rim portion.

In Example 4, the medical device of any one or any combination of Examples 1-3 may be configured such that wherein the rim portion of a slit seal directly contacts and seals against a bellows portion of the septum seal.

In Example 5, the medical device of any one or any combination of Examples 1-4 may further include a puck structure, the plurality of flaps and septum seal coupled to the puck structure.

In Example 6, thee medical device of any one or any combination of Examples 1-5 may be configured such that flexing of a bellows portion allows a puck structure, the flaps, and the septum opening to move to accommodate movement of an instrument inserted through the flaps and septum opening.

In Example 7, the medical device of any one or any combination of Examples 1-6 may be configured such that a puck structure includes a first puck part and a second puck part, the first puck part having a protrusion that extends through a second opening in the septum seal and engages the second puck part to couple to the first puck part to the second puck part and the septum seal.

In Example 8, the medical device of any one or any combination of Examples 1-7, may be configured such that the septum seal includes a reinforcement structure around the second opening.

In Example 9, the medical device of any one or any combination of Examples 1-8, may be configured such that a puck structure includes a lubrication channel extending from a top surface of the puck structure to a space between the plurality of flaps and the septum wall.

In Example 10, the medical device of any one or any combination of Examples 1-9, may be configured such that the septum seal includes a retaining structure that engages a puck structure to restrain movement of the septum wall with respect to the puck structure.

In Example 11, the medical device of any one or any combination of Examples 1-10 may further include a housing, wherein the septum seal, a slit seal, and a puck structure are in the housing.

In Example 12, the medical device of any one or any combination of Examples 1-11, may be configured such that the housing includes an upper housing part and a lower housing part coupled to the upper housing part.

In Example 13, the medical device of any one or any combination of Examples 1-12 may further include a cap between a bellows portion and the housing, wherein the cap inhibits inflation of the bellows portion in response to a pressure change.

In Example 14, the medical device of any one or any combination of Examples 1-13, may be configured such that the housing includes a guide portion sized and shaped to guide an instrument toward the septum opening, wherein the guide portion extends past the cap.

In Example 15, the medical device of any one or any combination of Examples 1-14 may be configured such that a slit seal includes a retaining structure that engages the housing to restrain movement of the slit seal.

In Example 16, the medical device of any one or any combination of Examples 1-15 may further include a cannula having a proximal portion sized, a distal portion, and an elongated body extending between the proximal portion and the distal portion, the proximal portion is shaped to receive the housing, wherein the housing is inserted into the proximal portion of the cannula.

In Example 17, the medical device of any one or any combination of Examples 1-16 may be configured such that the cannula includes a cannula bowl and the housing is in the cannula bowl, the cannula bowl extending past a most distal portion of the housing.

In Example 18, the medical device of any one or any combination of Examples 1-17 may be configured such that the most distal portion of the housing is less than three-fourths of the way into a cannula bowl.

In Example 19, the medical device of any one or any combination of Examples 1-18 may be configured such that the housing includes a guide surface that is sized and shaped to guide an object into the housing.

In Example 20, the medical device of any one or any combination of Examples 1-19 may further include a puck structure, wherein the puck structure, the septum seal, the plurality of flaps, a slit seal, and the lower housing part are coupled together.

In Example 21, the medical device of any one or any combination of Examples 1-20, may be configured such that a slit seal is adhered to the lower housing part and to the septum seal.

In Example 22, the medical device of any one or any combination of Examples 1-21 may be configured such that a puck structure, the septum seal, the plurality of flaps, a slit seal, and the lower housing part are provided as a disposable part and the upper housing part is reusable.

In Example 23, the medical device of any one or any combination of Examples 1-22, may be configured such that the lower housing part is sized and shaped to seal against a cannula.

In Example 24, the medical device of any one or any combination of Examples 1-23 may be configured such that the lower housing part is made of rubber.

In Example 25, the medical device of any one or any combination of Examples 1-24 may be configured such that the upper housing part is removably attached to the lower housing part.

In Example 26, the medical device of any one or any combination of Examples 1-25 may be configured such that the upper housing part is removable from the lower housing part by manually squeezing the upper housing part.

In Example 27, the medical device of any one or any combination of Examples 1-26 may be configured such that the upper housing part is oval shaped and squeezing an elongated portion of the upper housing part releases the upper housing part from the lower housing part.

Each of these non-limiting examples can stand on its own, or can be combined in various permutations or combinations with one or more of the other examples.

This Summary is intended to provide an overview of subject matter of the present patent application, It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Overview

A medical device (e.g., seal assembly) may include a septum seal and a plurality of flaps that extend over the septum seal. The flaps may protect the septum seal from puncture or damage when an instrument or other object is inserted through the seal. The flaps may come together to define an opening that overlaps with an opening in the septum seal. To facilitate assembly, the flaps may be separate pieces, which may be coupled to the septum seal.

The medical device may also include a bellows structure, to which the septum seal and flaps may be coupled. The bellows may allow for lateral movement of the septum and flaps via flexing of a corrugated region in the bellows. In some examples, the bellows may be connected to the septum seal. For example, the bellows and septum seal may be portions of a single part.

The medical device may also include a slit seal, such as a cross-slit seal. In some examples, the slit seal may be in direct contact with the septum seal, which may promote effective sealing of the device.

The medical device may include puck components, which may facilitate assembly. For example, the flaps may be coupled to a top puck part, and a bottom puck part may engage (e.g., extend through) the septum seal and couple to the top puck part to form a puck assembly that includes the flaps, bellows, septum seal, and top and bottom puck parts. One or more retaining structures (e.g., an anchoring ring) on the septum seal or slit seal may engage the top puck part or bottom puck part to retain relative movement of the components. The top puck part or bottom puck part may include a lubrication channel, which may for example allow for application of a lubricant on a surface of the septum seal.

The medical device may include a housing, or be contained within a housing. The housing may for example include an upper housing and a lower housing that couple together to capture the seals and other components in the housing. In some examples, a cap may be provided between the bellows and the upper housing to avoid movement (e.g., inflation) of the bellows through an access hole or other opening in the housing.

Example medical devices may be used with a telerobotically-controlled surgical system. For example, medical devices as described herein may be an instrument seal for use with a cannula that may be coupled to a patient at a surgical access site. An instrument, which may be manually-operated, or controlled using a telerobotic surgical system, may be inserted through the septum seal and slit seal and into a patient to perform a surgical procedure. The septum seal may seal against an instrument shaft when the instrument is inserted through the medical device. The slit seal may seal against itself when an instrument is not inserted, which may maintain an insufflation pressure in the patient.

Example System

Figure 1A:
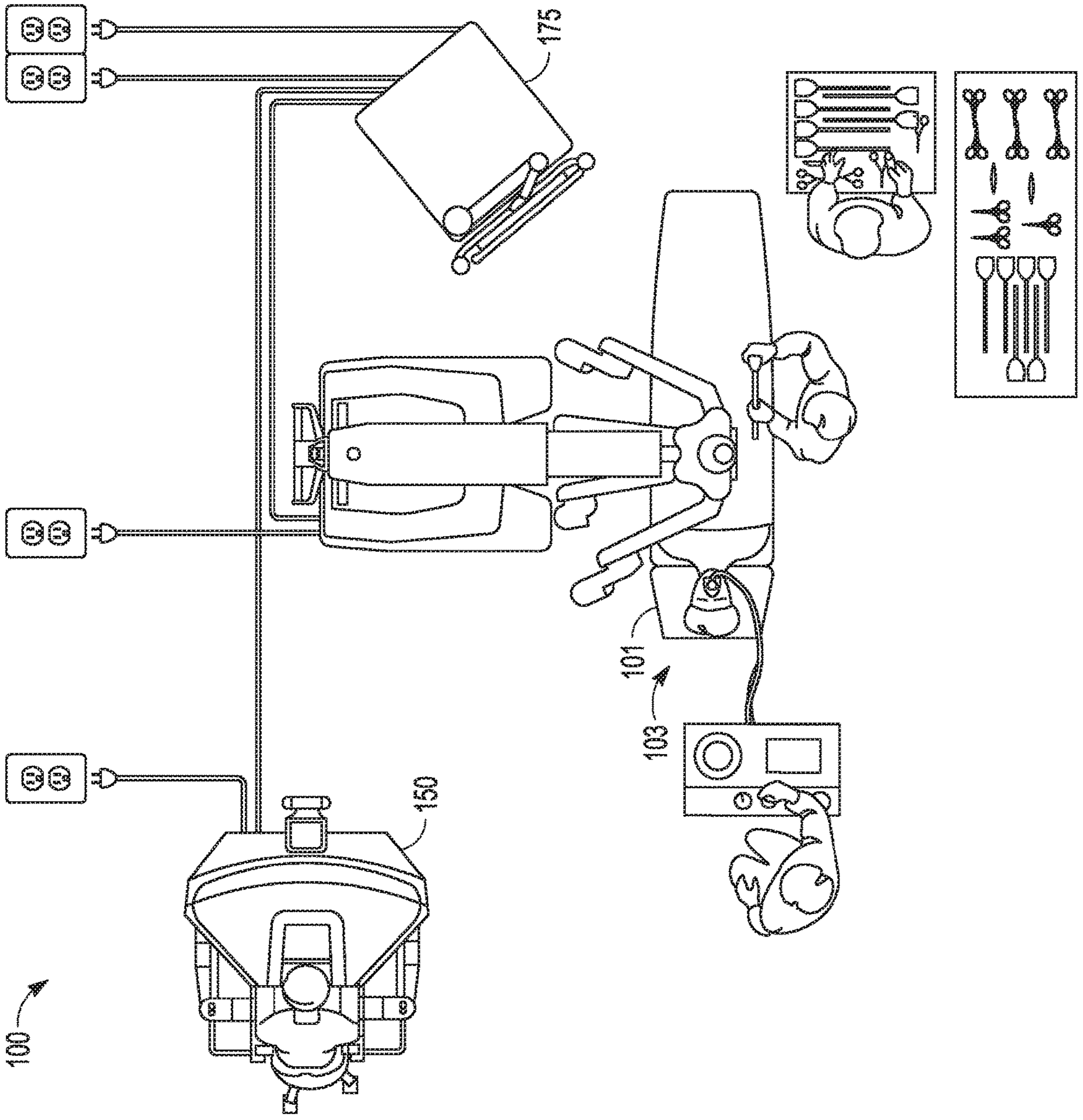
FIG. 1A is a plan-view illustration of an example medical system that may include a user control system, an auxiliary system, and a manipulating system.

FIG. 1A is a plan-view illustration of an example medical procedure environment in which the medical devices described herein may be used. The environment may include a multi-arm manipulating system 100 adjacent to a surgical table 101 that may support a patient 103.

The manipulating system 100 may be part of a larger system 10, which may include other sub-systems. For example, the manipulating system 100, may be operatively coupled to a user control system 150 or an auxiliary system 175, or both. The user control system 150 may include one or more user input devices (e.g., controls) that may be configured to receive inputs from a user (e.g., clinician). The user control system 150 may also include or one or more a user feedback devices (e.g., viewing system or tactile or auditory feedback) that may be configured to provide information to the user regarding the movement or position of an end effector, or an image of a surgical area. The auxiliary system 175 may, for example, include processing equipment (e.g., a processor circuit or graphics hardware) or communication equipment (e.g., wired or wireless communication circuits).

Figure 1B:
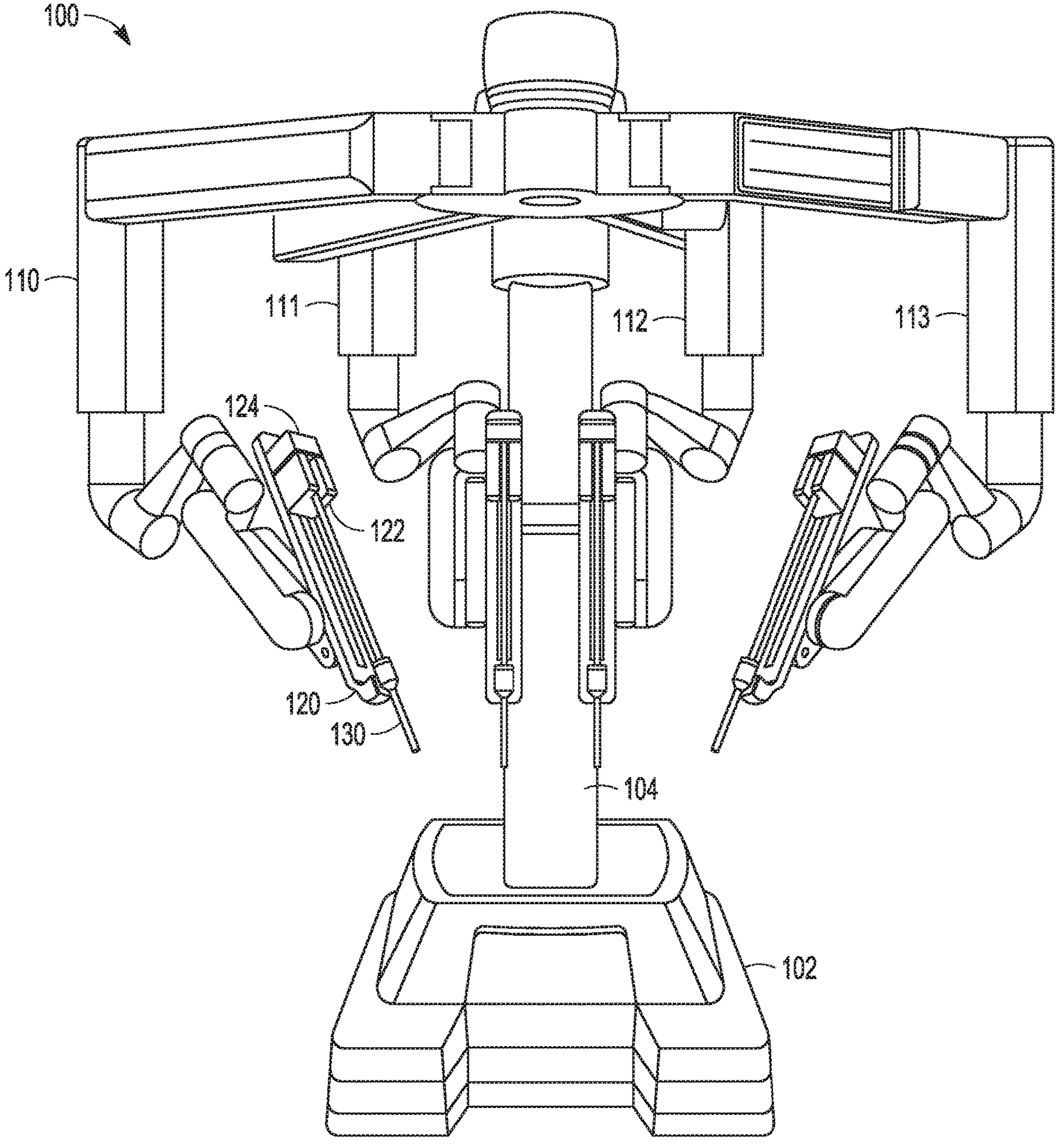
FIG. 1B is an illustration of an example manipulating system.

FIG. 1B is an illustration of example manipulating system 100. The manipulating system 100 may include a base 102, a support tower 104, and one or more manipulator arms 110, 111, 112, 113, which may be mounted on the support tower. An instrument 130 may be mounted to an instrument mount 120 on one of the manipulator arms. The instrument mount 120 may, for example, include an instrument carriage 122, which may be mounted to a spar 124, which may be a telescoping spar. A cannula may be mounted to a cannula mount 126, and an instrument 130 may be inserted through a cannula seal in the cannula, and into the patient 103 for use in a surgical or other medical procedure. Through movement of the manipulator arms, the orientation of the instrument may be controlled in multiple dimensions, e.g. lateral, horizontal, vertical, angular movements in one, two, or three planes.

Figure 1C:
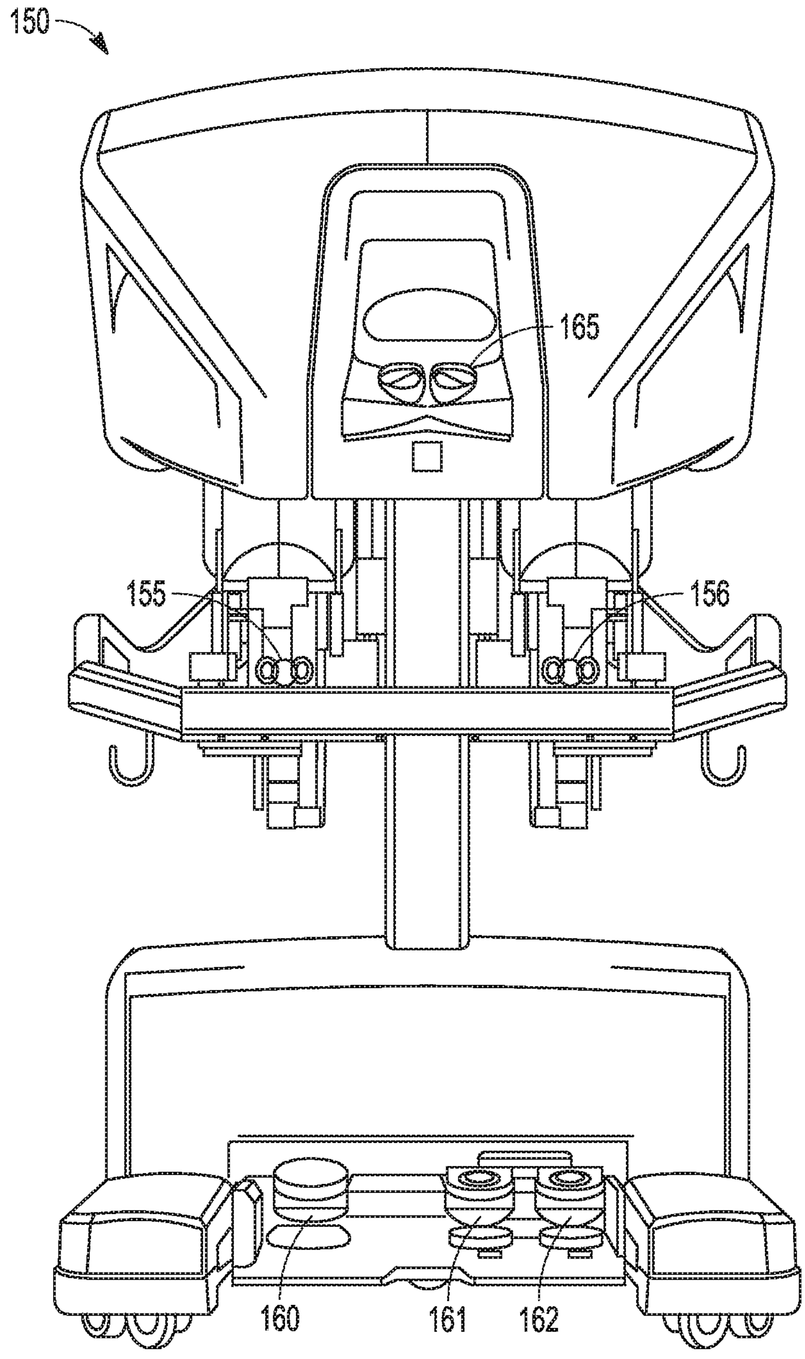
FIG. 1C is an illustration of an example user control system.

FIG. 1C is an illustration of example user control system 150. The user control system 150 may include hand controls 155, 156 and pedal controls 160, 161, 162. The hand controls 155, 156, and pedal controls 160, 161, 162 may be used to control equipment at the manipulating system 100. For example, portions of a distal end of an instrument 130 may be manipulated using the instrument controls. The controls may include haptic feedback features so that a physician may interpret physical information, such as resistance or vibration, through the controls. The user control system 150 may also include a viewing system 165 that may display video or other images of a surgical site.

Figure 1D:
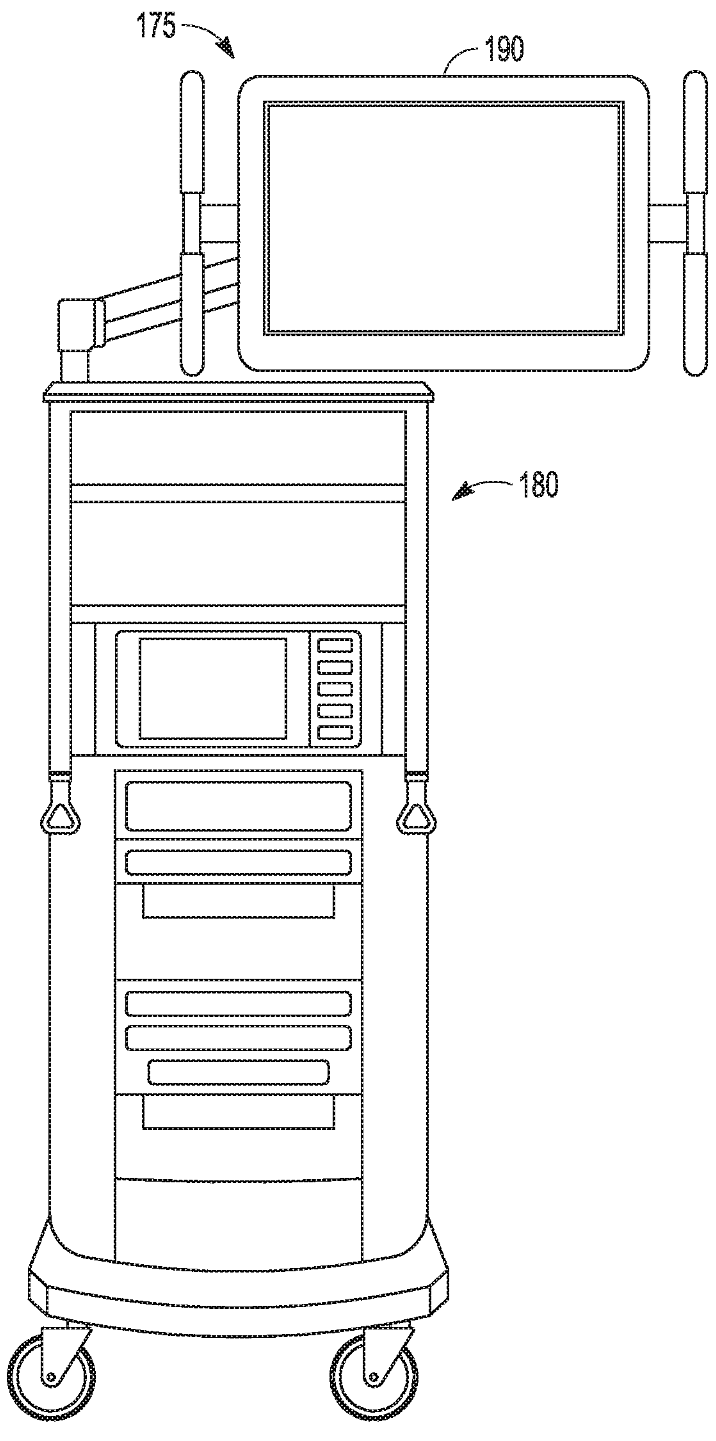
FIG. 1D is an illustration of an example auxiliary system.

FIG. 1D shows example auxiliary system 175. The auxiliary system 175 may include processing equipment 180 for processing controls, facilitating communication between the user control system and the manipulating system, or a remote site. The auxiliary system 175 may also include a display 190, which may show images that the user (e.g., clinician) is seeing on the user control system, a video feed from a camera in the patient, or other information. In an example configuration, signals input at a user control system 150 may be transmitted to the equipment 180 on the auxiliary system, which may interpret the inputs and generate commands that are transmitted to the manipulating system 100 to cause manipulation of an instrument 130 or portions of a manipulator arm 110. The equipment 180 is shown on a cart for exemplary purposes, but may also be arranged in various configurations, e.g., it may be integrated as part of the user control system, the manipulating system, or both, or divided between the user control system and manipulating system. The equipment may also be provided as software, hardware, or both, on an installed or remote system.

FIGS. 2A to 2H and 3A-3E show an example instrument seal 200. The seal 200 may include a plurality of flaps 202, 204, 206, 208 that may lie on top of one another and come together to form a flap opening 210. The flaps may, for example, be formed of polyurethane, such as 90 durometer polyurethane, which may provide desirable durability or flexibility characteristics. The flaps may be positioned over a septum seal 212. The septum seal 212 may be made of polyisoprene, such as a 43 durometer polyisoprene. The flaps may come together to form an opening 210 that is slightly larger an opening 217 in the septum seal. The flap opening 210 may, for example, be in the shape of a polygon (e.g., square) or may be round (e.g., circular or ovular) or may be irregular. The flap opening may advantageously be symmetrical around an instrument insertion axis to provide consistent frictional forces or consistent performance. An instrument shaft may be inserted through the flaps and the through the septum seal 212. The flaps 202, 204, 206, 208 may protect the septum seal from puncture or damage by an instrument as it is inserted through the septum seal.

The septum seal 212 may stretch to accommodate an instrument shaft that is larger than the opening 214 in the septum seal 212. The flaps my rotate distally to accommodate the instrument shaft during insertion. During retraction, the flaps may provide structural support to avoid excessive proximal movement or inversion of the septum seal, which may create undesirable friction characteristics or unsmooth movements. It may desirable to have consistent frictional forces during retraction (or insertion) to facilitate manual (e.g., by a clinician) movement of an instrument shaft or movement by a teleoperated surgical system. Excessive or inconsistent frictional forces may create confusion about whether an instrument or attached object has been caught or snagged on another object (which may need to be resolved prior to retraction) or whether the friction forces are due to variations in seal friction.

The illustrated example includes four flaps. Other examples may include more flaps (e.g., five, six, seven or more flaps) or fewer flaps (e.g., 3 flaps.) Increasing the number of flaps may reduce the size of gaps between a cylindrical instrument shaft and the contours of the opening formed by the flaps, but may increase friction between the instrument shaft and the flaps. Reducing the number of flaps (e.g., three flaps instead of four) may increase the size of gaps between the flaps and a cylindrical instrument shaft inserted through the flaps.

Figure 2A:
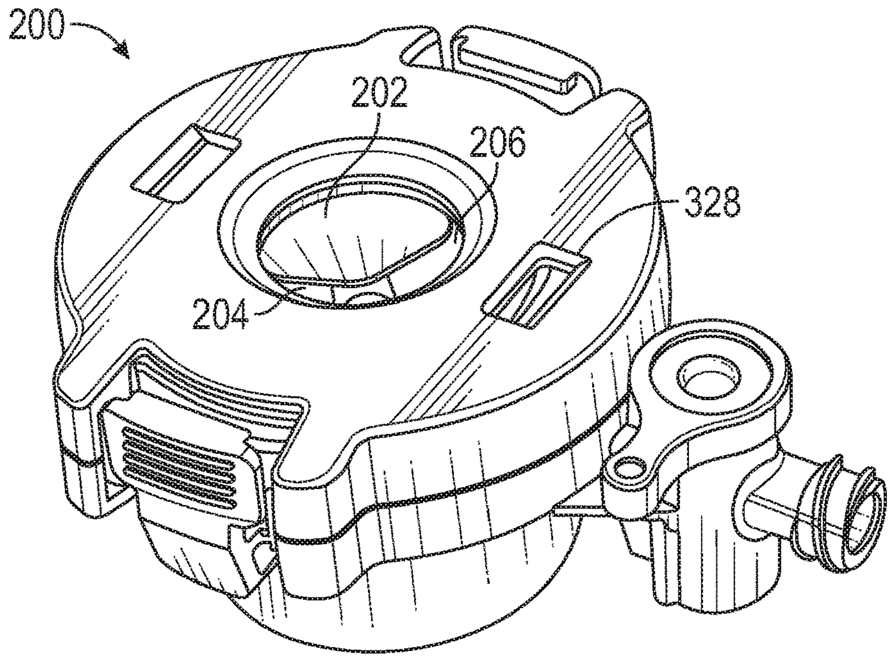
FIG. 2A is an illustration of an instrument seal.
Figure 2B:
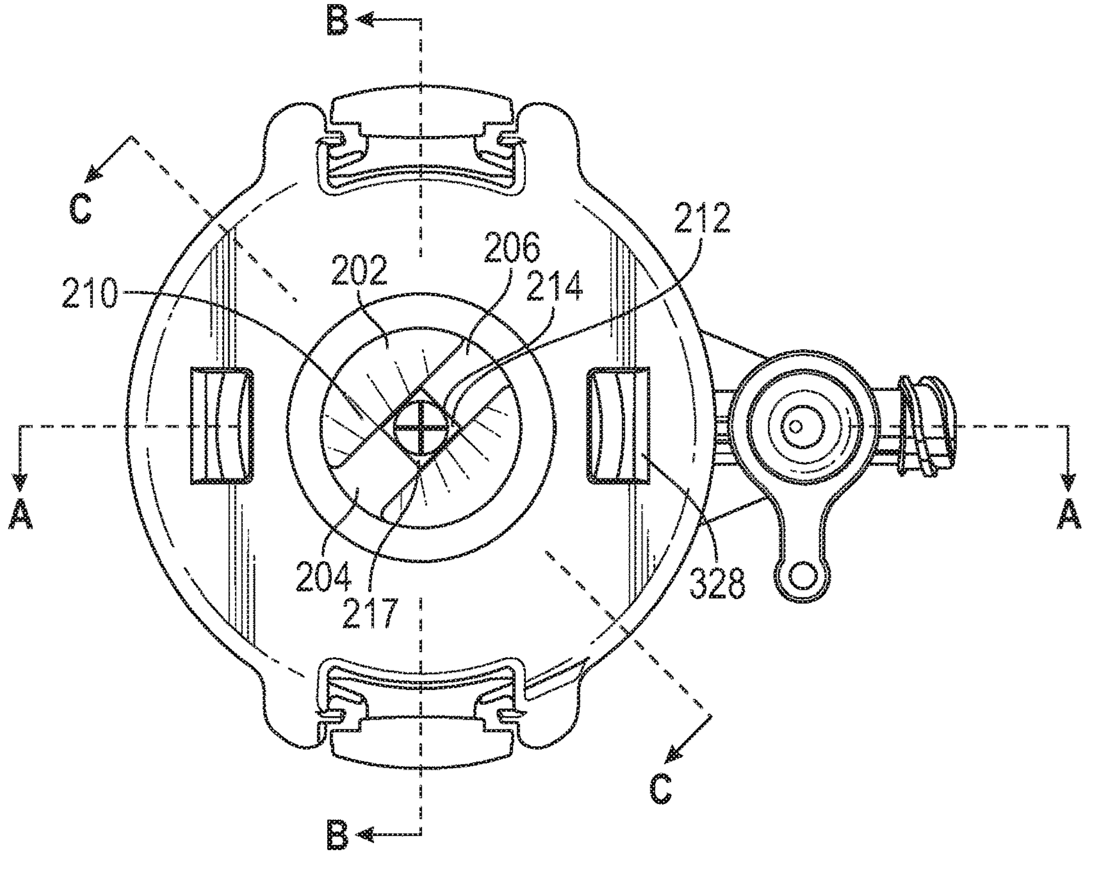
FIG. 2B is a top view of the instrument seal shown in FIG. 2A.
Figure 2C:
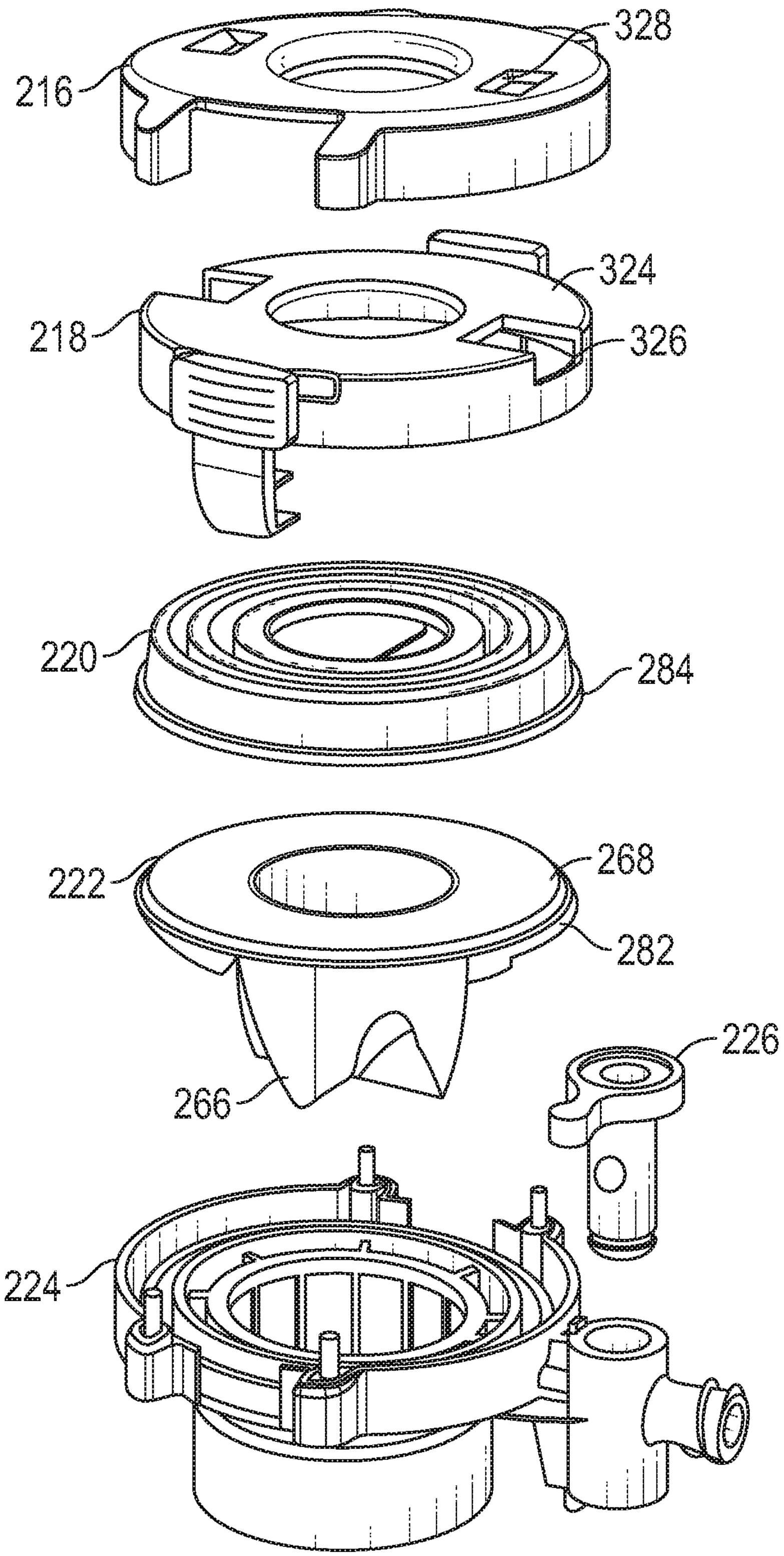
FIG. 2C is an exploded illustration of the instrument seal shown in FIGS. 2A-2B.

FIG. 2C is an exploded view of the seal 200. The seal may include an upper housing part 216, a latch 218, a puck assembly 220 (shown exploded in FIG. 2D), a slit seal 222 (e.g., cross-slit seal), a lower housing part 224, and stopcock 226, all of which may stack together to form the seal 200. The upper housing part 216 may be coupled to the lower housing part 224, for example using an ultrasonic welding process. The stopcock 226 may be used to control the flow of insufflation gas into the lower housing part 224.

Figure 2D:
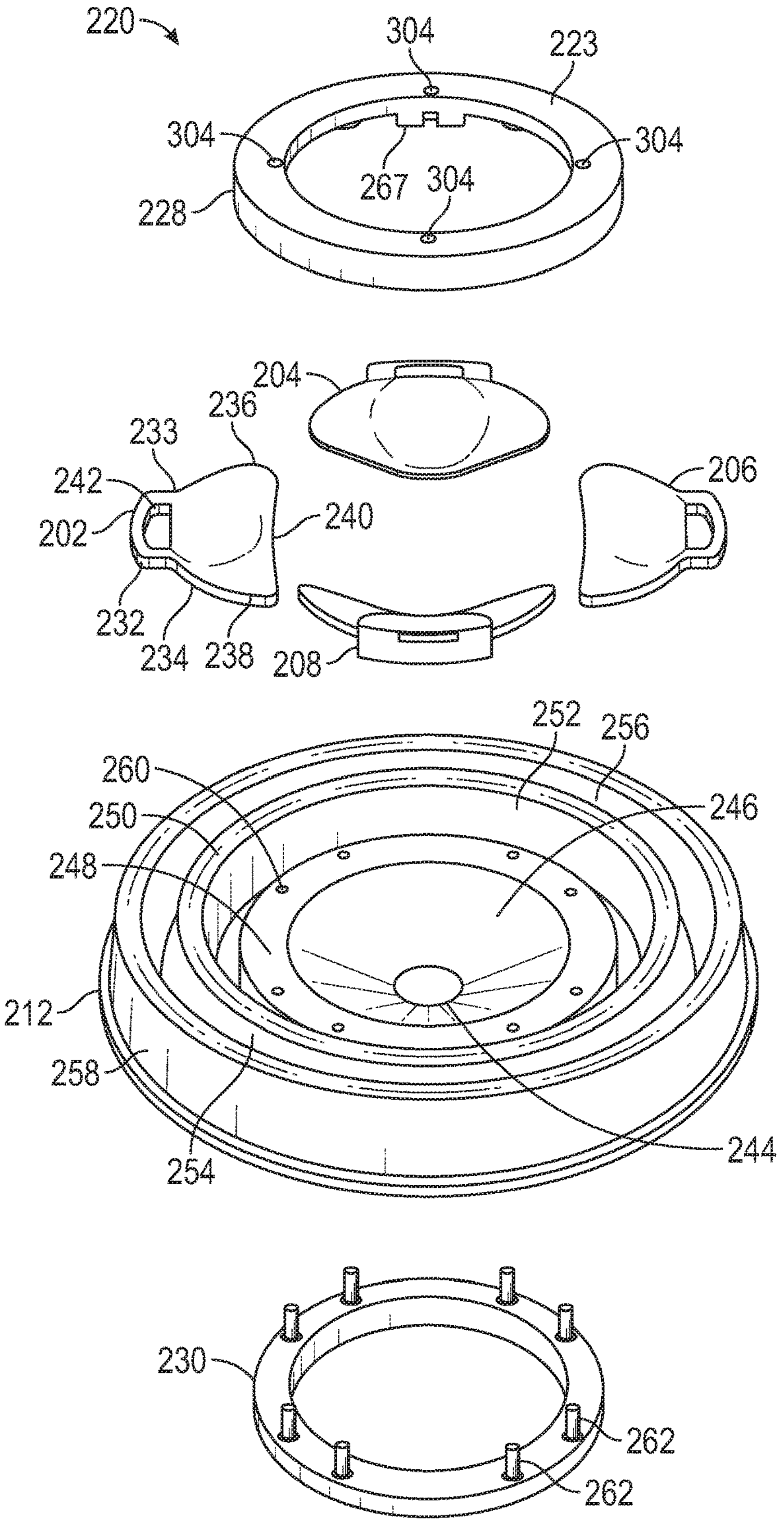
FIG. 2D is an exploded illustration of a puck assembly.
Figure 2E:
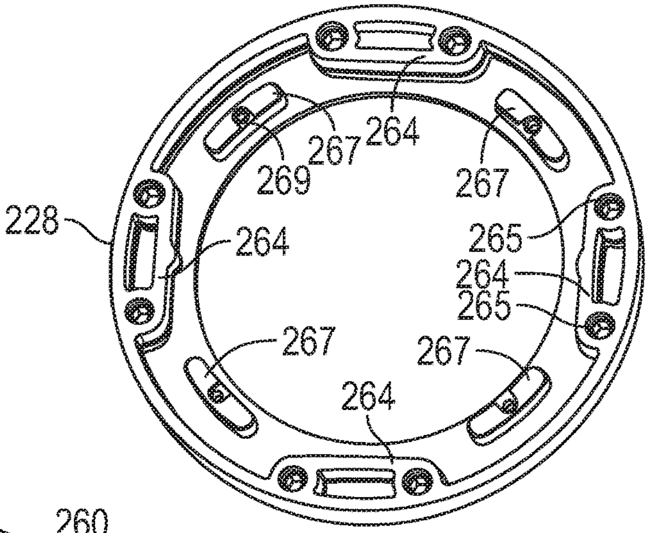
FIG. 2E is a bottom view of an upper puck part.

FIG. 2D is an exploded view of the puck assembly 220. The puck assembly 220 may include a puck structure, which may include an upper puck part 228 and a lower puck part 230, which may be coupled together using one or more retaining features (e.g., pins) as further described below. The puck structure may be round (e.g., circular or ovular), polygonal (e.g., triangular, square or pentagonal), or irregular. The puck assembly 220 may also include the flaps 202, 204, 206, 208 and the septum seal 212. As shown in FIG. 3B, when the puck assembly is assembled with the other components of the seal 200, an upper surface 223 on the upper puck part 228 may be adjacent (e.g. touching or next to) or spaced from the cap portion 324 of the latch 218 (shown in FIG. 3B), and lower surface 225 (labeled in FIG. 3B) of the lower puck part 230 may be adjacent to or spaced from the rim portion 268 of the slit seal.

As shown in FIG. 2D, a flap 202 (or any or all of the flaps) may include a flange portion 232 and a flap portion 234, which may extend distally and centrally (toward an instrument insertion axis). The flap portion 234 may be connected to the flange portion by a flexure portion 233, which may bend or flex to allow the flap portion 234 to move downward, e.g., when an instrument is inserted through the seal 200. The flap portion 234 may be shaped (e.g., cupped) so that the flaps fit together to form a 3-D curved surface. For example, flap side portions 236, 238 may be curved upward (proximally) from a center section 240 of the flap. A flap may also include one or more openings 242 for coupling the flap to another part. The opening 242 may be in the flange portion 232 of the flap. In some examples, the seal 200 may include a plurality of flaps (e.g., three, four, five, or more) that are each configured with one or more openings and a shaped flap portion. The plurality of flaps may be identical, or may different from each other.

The septum seal 212 may include a septum portion 243 that includes a septum wall 244, which may define an opening 246, which may seal against an instrument shaft inserted through the opening 246. The septum seal 212 may also include a rim portion 248. The septum wall 244 may extend distally (e.g., form a frustum) from the rim portion 248 to the opening 246 to guide an instrument toward the opening. The septum seal 212 may also include a bellows portion 250, which may include a plurality of corrugated walls 252, 254, 256, 258. The bellows portion may allow side-to-side movement (e.g., perpendicular to an instrument insertion axis) of the puck assembly 220, which may protect the septum portion 243 of the septum seal 212 as an instrument is manipulated in a cannula or allow for greater range of motion or easier movement of an instrument shaft by a clinician or by a teleoperated surgical system controlled by a clinician.

Figure 2F:
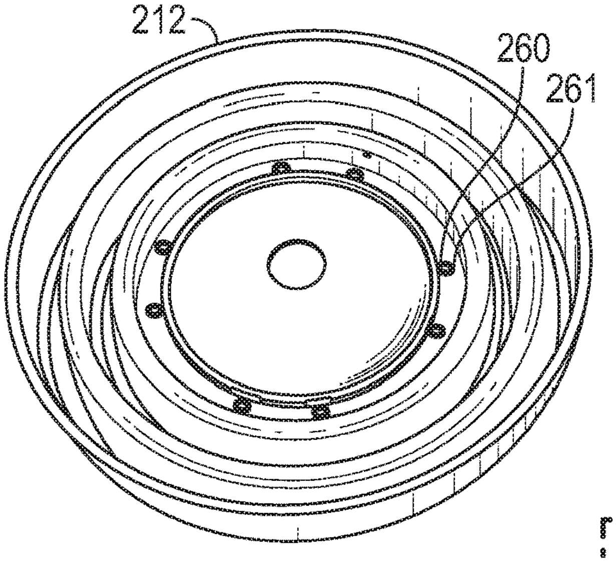
FIG. 2F is a bottom view of a septum seal.
Figure 2G:
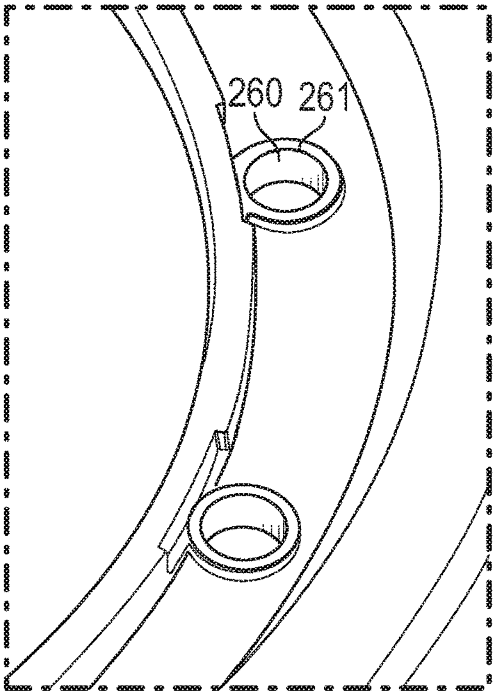
FIG. 2G is an enlarged view of the bottom of the septum seal.

The rim portion 248 may include one or more openings 260, which may be surrounded by a reinforcing structure 261 (e.g., a ring) as shown in FIGS. 2F and 2G. The lower puck part 230 may include one or more protrusions 262, which may be sized and shaped to extend through an opening 260 in the septum seal and into a corresponding opening 265 in a receiving portion 264 of the upper puck part 228 (shown in FIG. 2E). The opening 265 may be sized and shaped to provide a press-fit, snapfit, or ultrasonic weld interface with the protrusion 262 to retain the assembly of the upper puck part, flap(s), septum seal 212 and lower puck part 230 together. In some examples, the lower puck part 230 may have a plurality of pairs of protrusions 262 (e.g., pins), that may each be sized and shaped to extend through corresponding openings 260 in the septum seal 212 into a receiving portion 264 on the upper puck part 228, as shown in FIG. 3D. The reinforcing structures 261 on the septum seal 212 may provide local structural support at locations around the protrusions 262. In an alternative configuration, the upper puck part 228 may include protrusions and the lower puck part 230 may include receiving portions configured to receive the protrusions, or both the upper and lower puck parts 228, 230 may include protrusions and receiving portions aligned with the protrusions on the other puck part to couple the puck parts together.

The construction of the puck assembly from the septum seal 212 with connected bellows portion 250, flaps, 202, 204, 206, 208 and upper and lower puck parts may advantageously provide a simple assembly procedure and simple overall puck assembly architecture. For example, forming the septum portion 243 and bellows portion 250 in a single part avoids a need to align the septum portion and bellows portions (as would be required if they were separate parts.) The assembly process may also be advantageously simple. For example, the septum seal 212 may be assembled over the lower puck part 230 with the protrusions 262 (e.g., pins) extending through the openings 260 in the septum seal 212. The flaps 202, 204, 206, 208 may assembled onto protrusions 267 (shown in FIG. 2E) on the bottom side of the upper puck part 228, with a protrusion 267 extending through the opening 242 in a flap. The flap may be optionally retained with a retainer part such as a clip (not shown), a portion of which may extend into a hole 269 in the protrusion 267. As previously described, the upper puck part 228 may be coupled to the lower puck part 230 by inserting the protrusions 262 into holes in the receiving portions 264 of the upper puck part 228, which holds the upper puck part 228, lower puck part 230, flaps 202, 204, 206, 208 and septum seal 212 together to form the puck assembly 220.

The puck assembly 220 may be assembled on top of the slit seal 222, as shown in FIG. 2C and 3A-D. The slit seal 222 may include a seal portion 266 and a rim portion 268. The seal portion may, for example, be a cross-slit seal, single-slit, or a tri-slit seal. The slit seal may include folded sidewalls that come together to form a slit.

In some examples, the septum seal 212 may directly contact the slit seal 222. For example, the bellows portion 250 of the septum seal 212 may rest against the rim portion 268 of the slit seal. The seal-to-seal contact may create a seal to avoid leakage. The direct seal-to-seal contact may be advantageous for sealing, e.g., because the seal-to-seal contact (e.g., rubber (polyisoprene) to rubber contact) may provide a better sealing of the components than if another part (e.g., plastic or polycarbonate) was between the seals. The septum seal 212 may be sized and shaped to fit over the slit seal 222. The slit seal 222 may include an outer lip 282, which may rest against an outer lip 284 on the septum seal (as shown in FIG. 3C.)

Figure 2H:
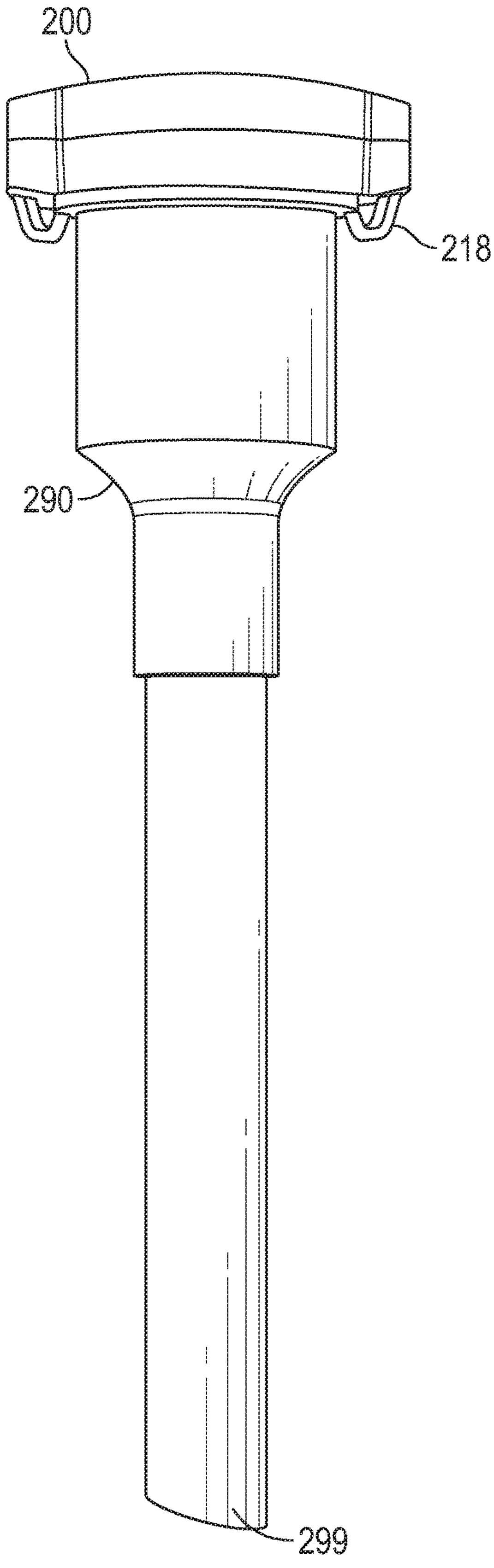
FIG. 2H is an illustration of an instrument seal on a cannula.

The seal 200 may be assembled onto a cannula 290, as shown in FIG. 2H. The cannula 290 may be coupled to the seal by the latch 218. The seal 200 may be used with a dockless cannula, as shown in FIG. 2H, or may alternatively be used with a dockable cannula, such as the cannula 406 shown in 4D, which may include a blade 408 for docking the cannula to a portion of a teleoperated surgical system.

Figure 3A:
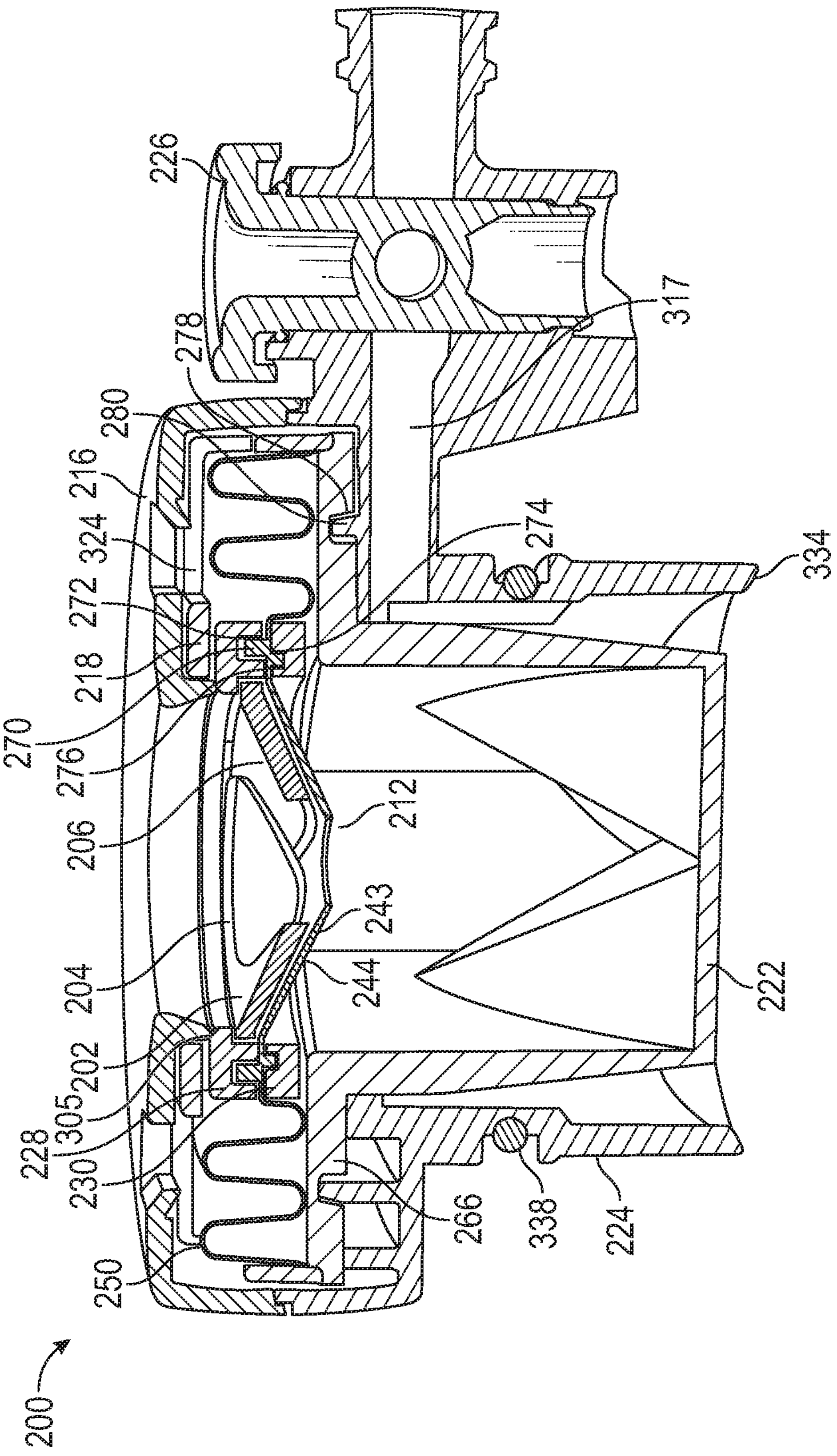
FIG. 3A is a cross-sectional view of the instrument seal shown in FIGS. 2A-2B.
Figure 3B:
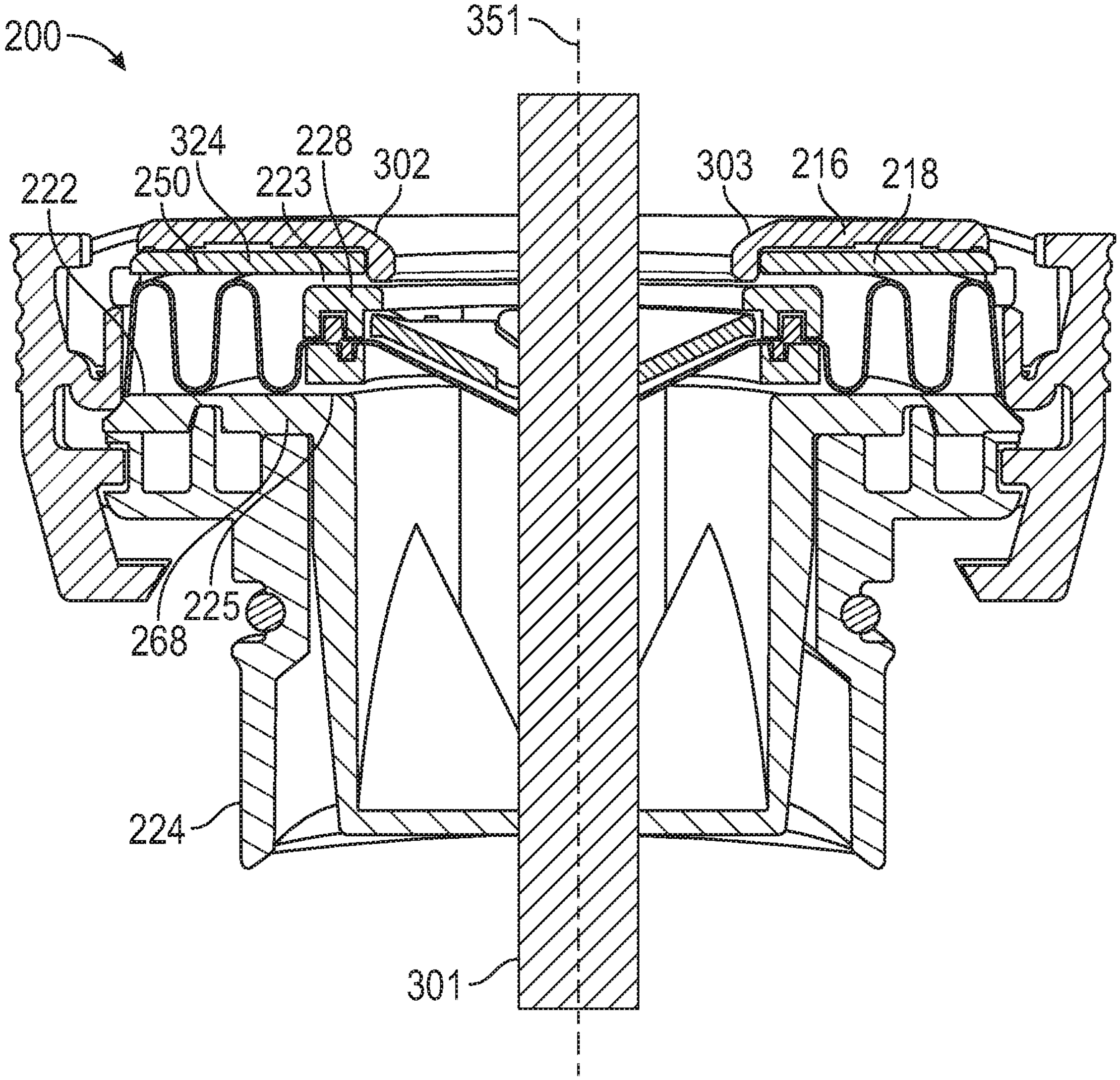
FIG. 3B is a cross-sectional view of the instrument seal shown in FIGS. 2A-2B.
Figure 3C:
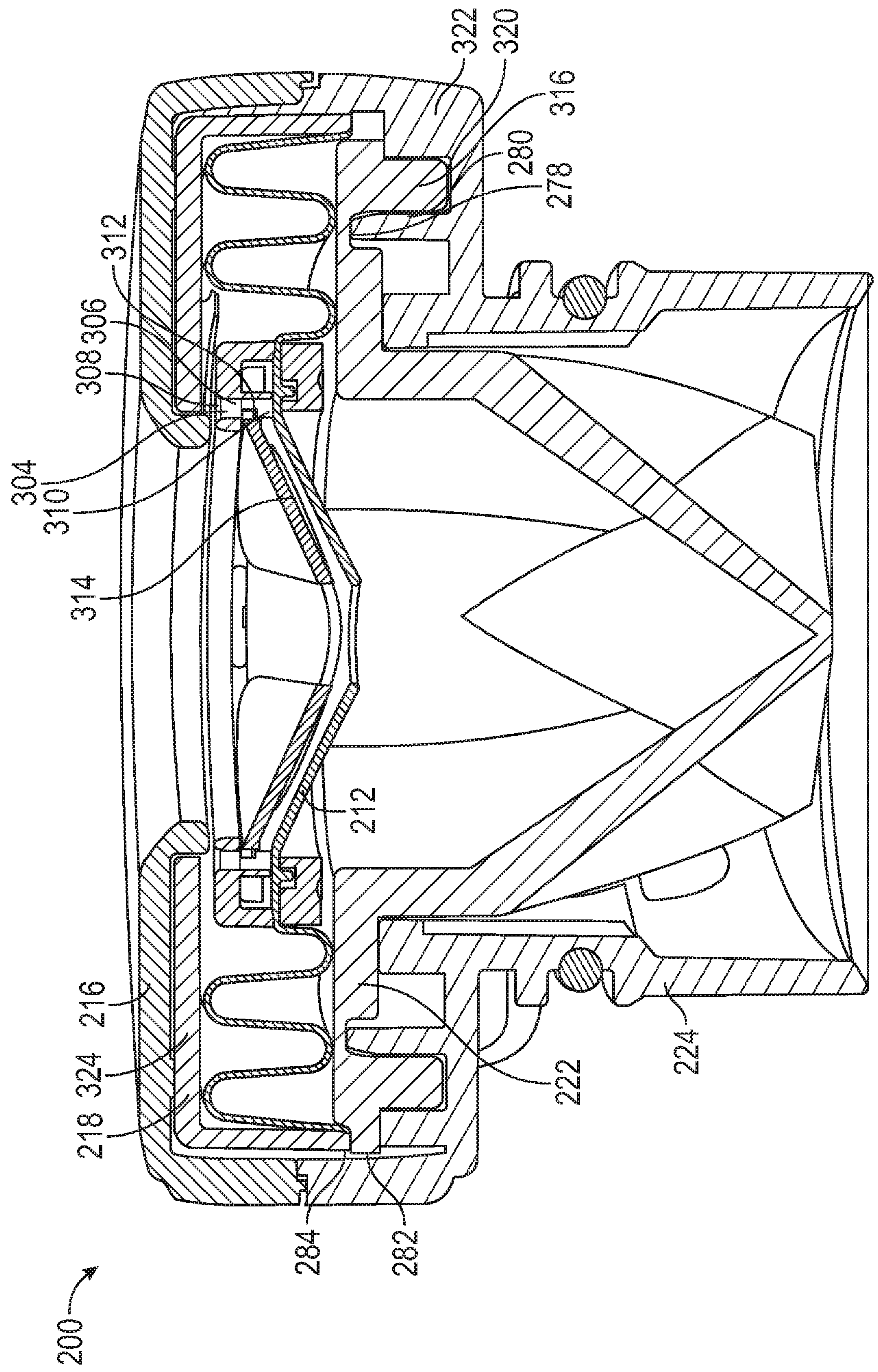
FIG. 3C is a cross-sectional view of the instrument seal shown in FIGS. 2A-2B.
Figure 3D:
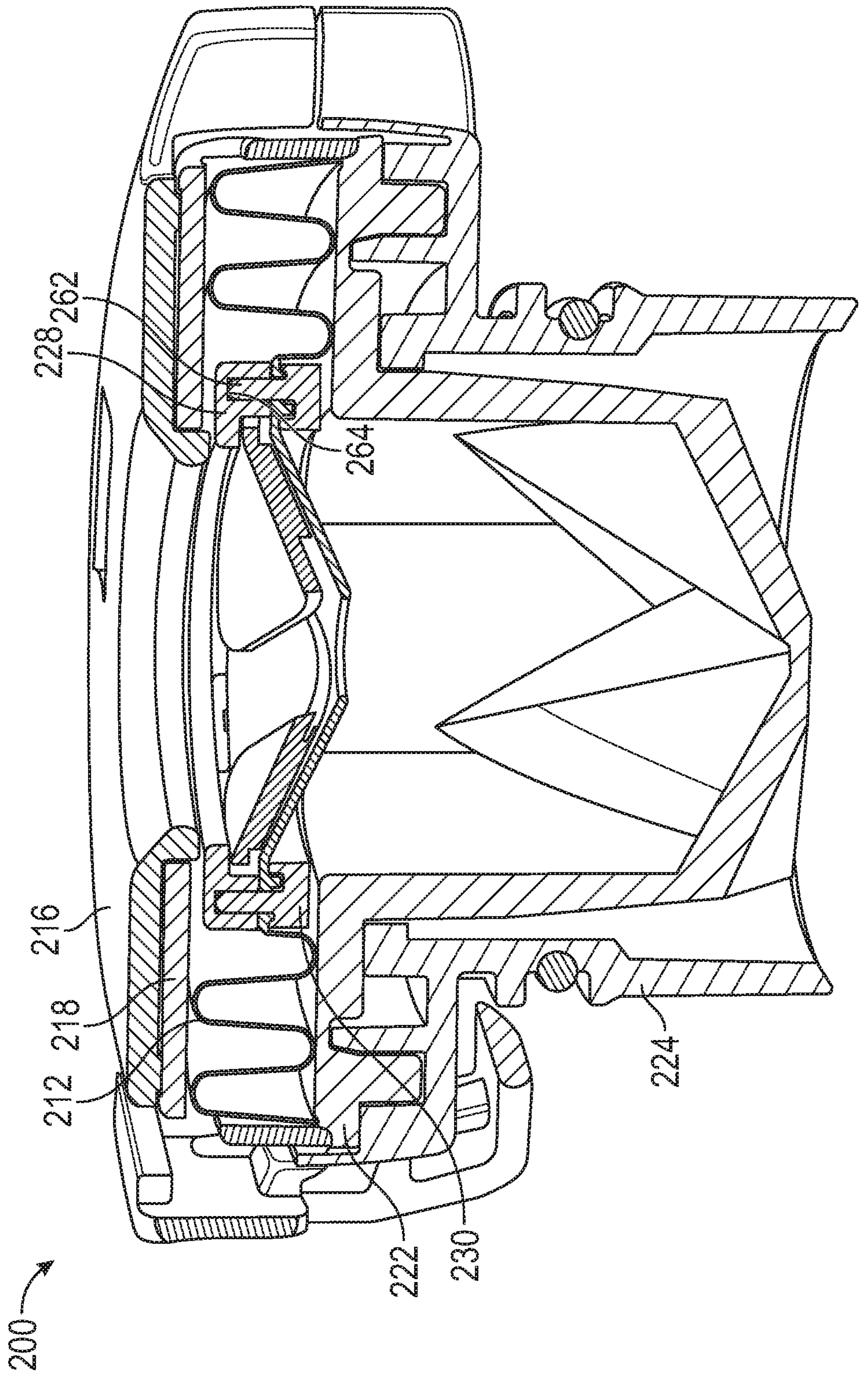
FIG. 3D is a cross-sectional view of the instrument seal shown in FIGS. 2A-2B.

FIG. 3A is a cross-sectional view of the seal 200 at section A-A shown in FIG. 2B. The septum seal 212 may optionally include an upper retaining structure (e.g., ring) 270, which may be sized and shaped to extend into a corresponding groove 272 on the upper puck part 228. The septum seal 212 may additionally or alternatively include a lower retaining structure (e.g., ring) 274 that may extend into a groove 276 on the lower puck part 230. The slit seal 222 may have a portions defining receiving space (e.g., groove) 278, which may receive a protrusion 280 on the lower housing part 224.

The upper retaining structure 270 or lower retraining protrusion 274 may avoid displacement of the septum seal 212 toward the center of the seal 200 when an object is inserted or withdrawn through the septum seal 212.

FIG. 3B is a cross-sectional view of the seal 200 at section B-B, shown with an instrument shaft 301 inserted along an insertion axis 351 through the flaps and septum seal 212. The flaps 202, 206, 208 may pivot downward (distally) to make room for the instrument shaft 301. The opening 214 in the septum seal 212 may stretch to accommodate the instrument shaft. The upper housing part 216 may include an instrument guiding portion 302 that may be sized and shape to guide an instrument toward the opening 214 in the septum seal. The instrument guiding portion 302 may extend distally past the latch 218, which may help avoid snagging of an instrument on a gap between the puck assembly 220 and the latch 218. In some examples, the instrument guiding portion 302 may include a lead-in channel 303 as shown in FIG. 3B. In some examples, the instrument guiding portion 302 may optionally contact the upper puck part 228 at an upper engagement surface 305.

FIG. 3C is a cross-sectional view of the seal 200 at section C-C. The seal 200 may include a lubrication path 304 through one or more of the components. For example, the upper puck part 228 may have a passageway 306, which may include an upper opening 308 in the top of the upper puck part and a lower opening 310 that joins a space 314 between the flaps and the septum portion 343 of the septum seal 212. A lubricant may be injected into the upper opening 308, and the lubricant may travel through a passageway 312 in the upper puck part to the lower opening 308, into the space 314 between the flaps 202, 204, 206, 208 and the septum wall 244. Placing the lubricant beneath the flaps may assist with avoiding smudges on an optical component (e.g., lens) of a camera instrument inserted through the seal. In some examples, the lubricant may be injected into the puck assembly 220 before assembly of the latch 218 and upper housing part 216 on top of the puck assembly 220. The puck assembly may include a plurality of lubrication paths 304 via a plurality of openings in the upper puck part 228 (as shown in FIG. 2D) to provide for distribution of lubrication to different locations on top of the septum portion 243 of the septum seal (e.g., to cover most or all of the septum portion with lubricant.)

The rim portion 268 of the slit seal 222 may include one or more retaining structures 316 (e.g., protrusion such as annular ring) sized and shaped to engage the lower housing part 224. For example, the retaining structure 316 may extend downward (distally) from the bottom side 318 of the rim portion and extend into a receiving space 320 (e.g., groove) on the lower housing part 224. The receiving space 320 may be defined by protrusion 278 and a second protrusion 322 on the lower housing part. The protrusion 316 may be a continuous ring, or may be segmented (e.g., include a gap in a ring) to accommodate an insufflation channel 317 (shown in FIG. 3A). The protrusion 316 may avoid slippage of the slit seal 222 toward the center of the seal when an object or instrument is inserted or withdrawn through the slit seal 222.

As shown in FIGS. 3A-3C, a cap portion 324, which may be connected to or part of the latch 218, may extend over the top of the bellows portion 250 of the septum seal. The cap portion 324 of the latch may inhibit inflation or distortion of the bellows portion 250 in response to a sudden pressure change, e.g., when an object is inserted through the septum. The cap portion 324 may include a cut-away portion 326, which may align with openings 328 in the upper housing part. The openings 328 may be sized and shaped to latch with another device. The presence of the cap portion 324 between the bellows portion 250 and the upper housing part 215 may provide more space (e.g., clearance) for a latch part (not shown) inserted through the openings.

Figure 3E:
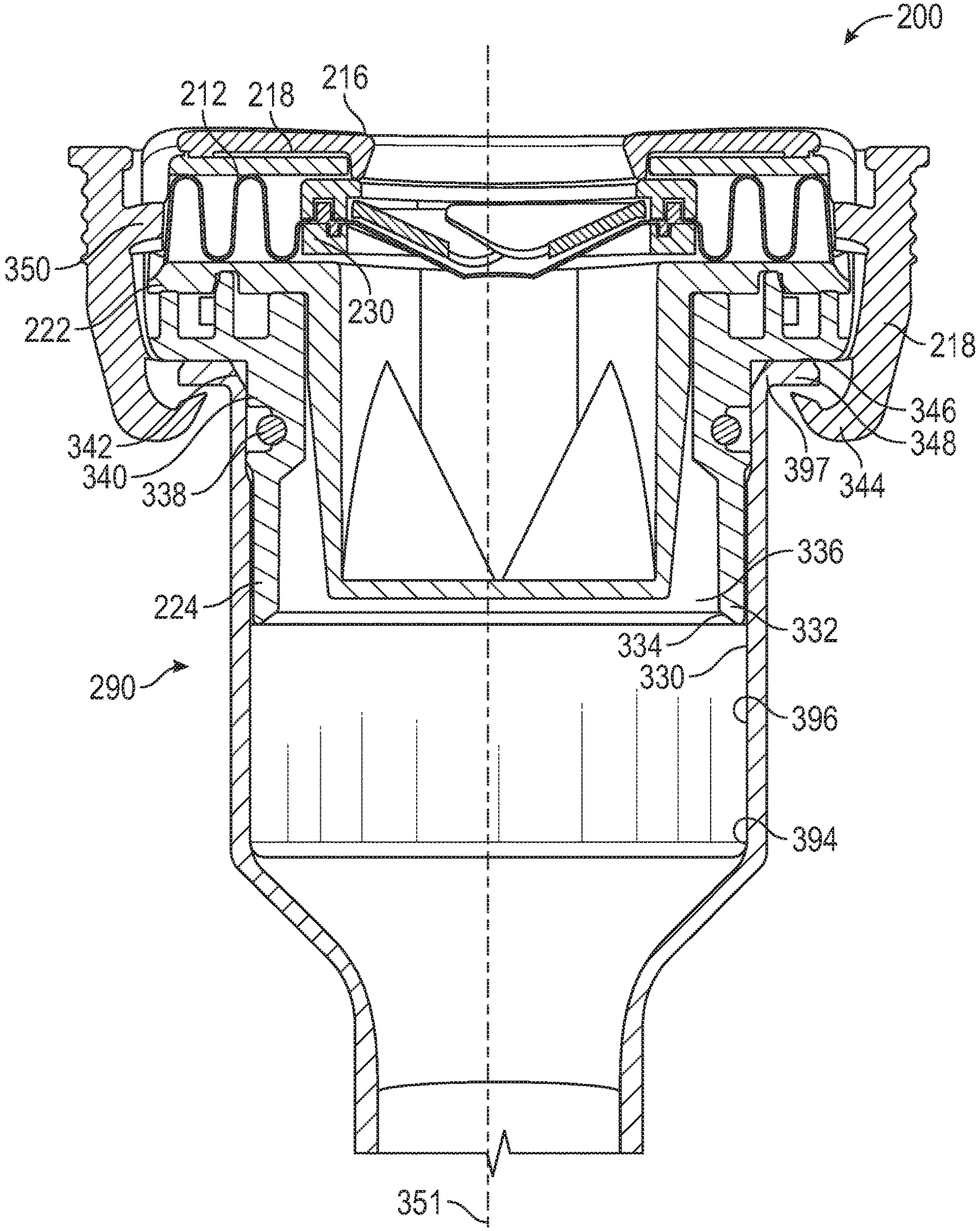
FIG. 3E is a cross-sectional view of the instrument seal shown in FIGS. 2A-2B engaged on a cannula.

FIG. 3E shows a seal 200 assembled with a cannula 290 having a proximal portion 397 sized and shaped to engage with the seal 200 and a distal portion 299 (shown in FIG. 2H) sized and shaped to couple to a patient to facilitate delivery of a surgical instrument. The lower housing part 224 may extend into a cannula bowl 396 at the proximal portion 397 of the cannula 290. In some examples, a small gap may exist between the lower housing part 224 and an inside wall 330 of the cannula 290, e.g., due to manufacturing tolerances and the need to fit the lower housing part inside the cannula. The cannula bowl 396 may extend past the lower housing part 224, e.g., the lower housing part 224 and septum may not extend to the bottom 394 of the cannula bowl 396. For example, the lower housing may extend less than three-fourths (75%) of the way into the cannula bowl, or may extend less than half (50%) of the way into the cannula bowl. To facilitate withdrawal of an object (e.g., instrument) into the lower housing part 224 and seal portion 266 of the slit seal 222, a distal portion 332 of the lower housing part 224 may include an extraction guide surface 334 that may be sized and shaped (e.g., angled toward an insertion axis 351) to guide an instrument or other object into an inner cavity 336 of the lower housing part or toward the seal portion 266 of the slit seal.

A seal such as an O-ring 338 may form a seal between the lower housing part 224 and the cannula 290. In some examples, the lower housing part 224 may include a channel 340 that extends around an outer surface 342 of the lower housing part 224 and the O-ring (or other seal) may be in the channel and extend radially outward past the outer surface 342 so that the inner wall 330 of the cannula 290 seals against the O-ring 338. In some examples, the O-ring 338 may retain the lower housing part 224 in the cannula 290.

In some examples, the latch may 218 may also retain the seal 200 to the cannula 290. For example, a lower portion 344 of the latch 218 may be sized and shaped to engage an engagement feature (e.g., lip) on the cannula 290. In some examples, the latch may be spaced (as shown) from the lip to prevent the seal 200 from separating from the cannula 290 if the lower housing part slips upward in the cannula 290. In some examples, the lower portion 344 of the latch may be formed with a hook shape to reach below the engagement feature and engage an underside 348 of the engagement feature. The latch may include an inwardly-extending protrusion 350 that may avoid movement of the outer wall 258 of the bellows portion 250 from moving out the side of the cannula.

Figure 4A:
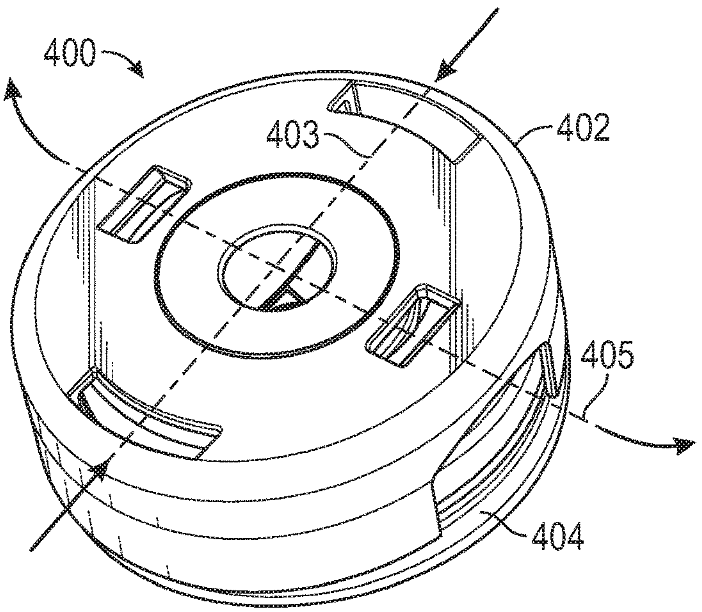
FIG. 4A is a perspective view of an example seal.

FIG. 4A shows another example seal 400. The seal 400 may include a cap 402, which may be reusable, and a bottom portion 404, which may be disposable. In some examples, the seal 400 may be designed as a low-cost seal. The seal 400 may not include an insufflation gas passage and stopcock (as shown in FIG. 4A), which may reduce the cost, or the seal 400 may optionally include an insufflation gas passage and stopcock, such as shown in FIG. 2A-C.

Figure 4B:
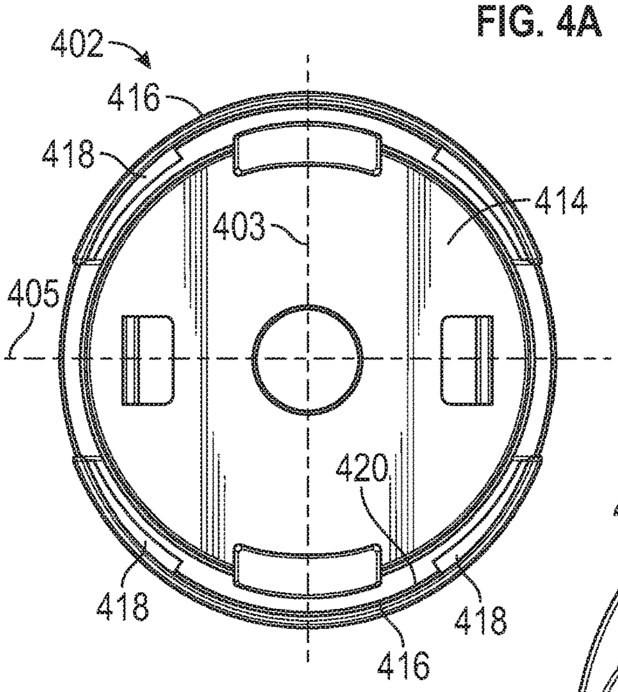
FIG. 4B is an a bottom view of an example seal cap.
Figure 4C:
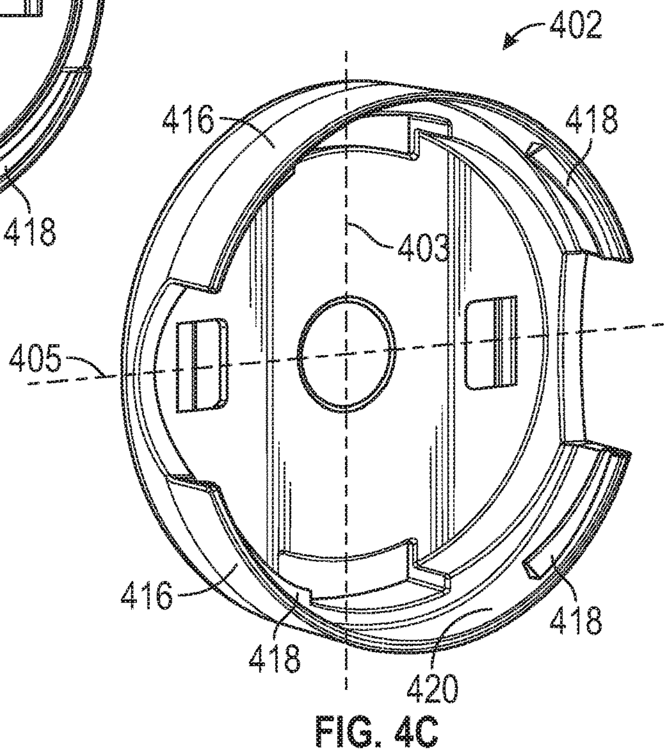
FIG. 4C is a perspective view of the seal cap shown in FIG. 4B.
Figure 4D:
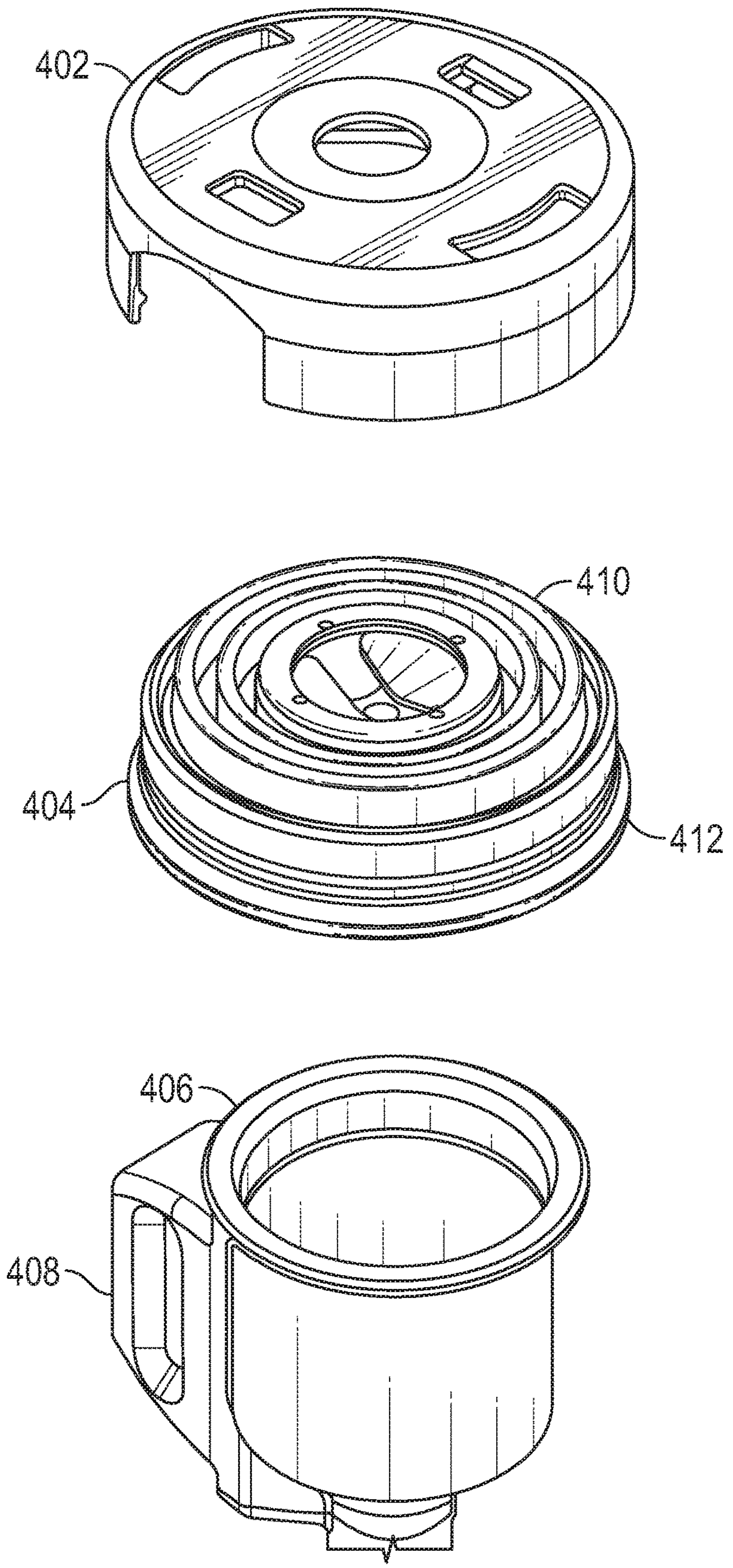
FIG. 4D is an exploded perspective view of the example seal shown in FIG. 4A and a cannula with which the seal may be used.

FIG. 4D is an exploded perspective view of the example seal 400 shown in FIG. 4A and a cannula 406 with which the seal 400 may be used. The cap 402 may be assembled onto the bottom portion 404, and the assembled seal 400 may be coupled to the cannula 406, for example as shown in FIG. 4F.

As shown in FIGS. 4B and 4C, the cap 402 may have an elliptical or oblong shape having a long dimension (e.g., along a major axis 403) and a short dimension (e.g., along a minor axis 405), which may allow for assembly and disassembly with the bottom portion 404 by squeezing along a major axis (longer dimension) of the cap. The cap may include a top portion 414, one or more side portions 416, and one or more ridges 418 on an inner surface 420 of the side portions. The ridges 418 may have a tapered height that decreases toward the minor axis 405. The ridges may engage one or more engagement features 422 (e.g. a groove or lip) on the bottom portion 404 (as shown in FIG. 4F). Squeezing the cap along the major axis (as indicated by arrows in FIG. 4A) may cause the ridges 418 to move outward (as indicated by arrows), which may allow the ridges to be engaged or disengaged with the engagement feature 422 on the seal. In this manner, the cap 402 may be assembled with the bottom portion 404, and, after use, disassembled from the seal portion, so that the bottom portion 404 may be disposed of or recycled and the cap 402 may be kept and reused (e.g., sterilized and attached to a new seal for use in another procedure.)

Figure 4E:
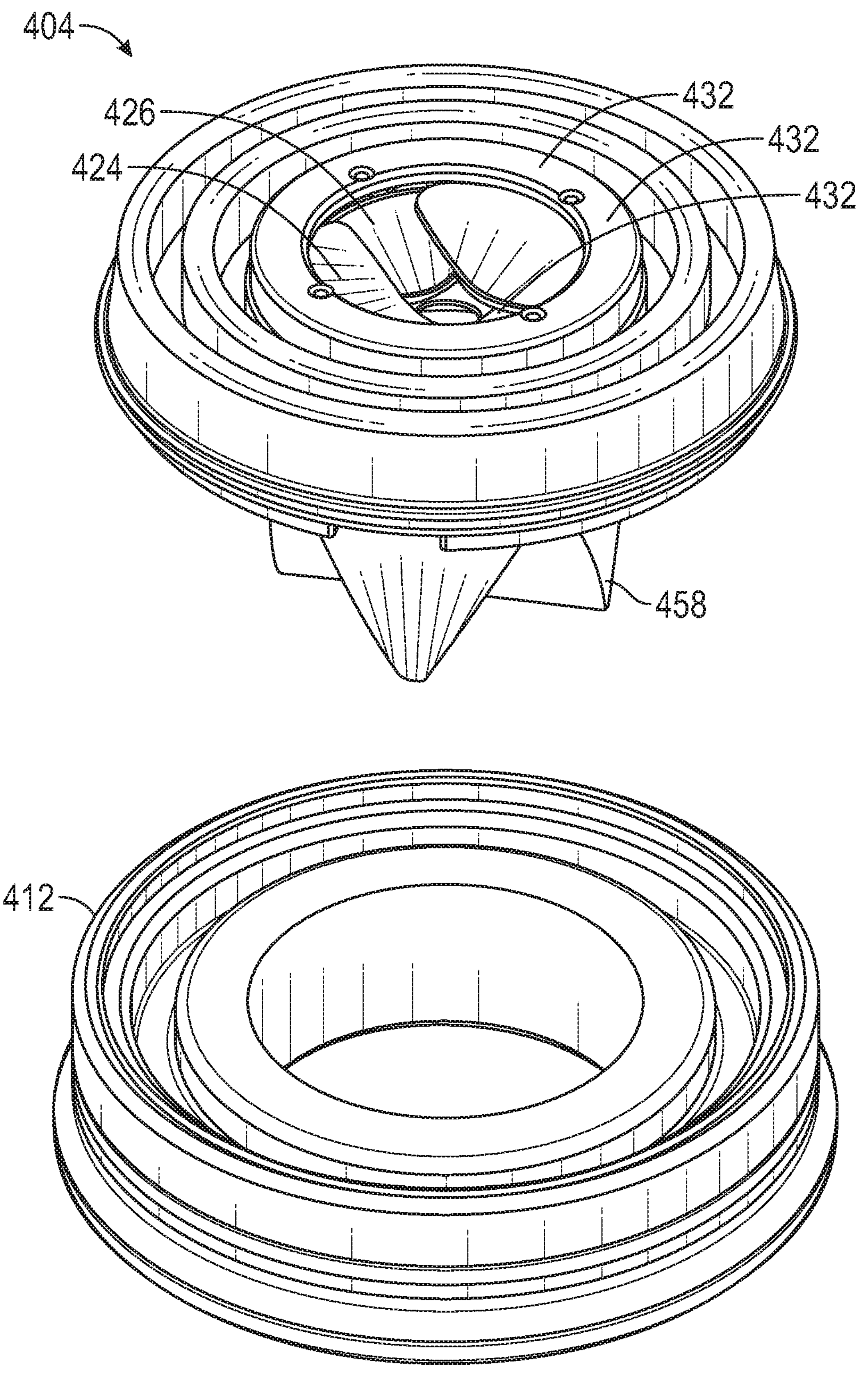
FIG. 4E is an exploded view of an example seal.
Figure 4F:
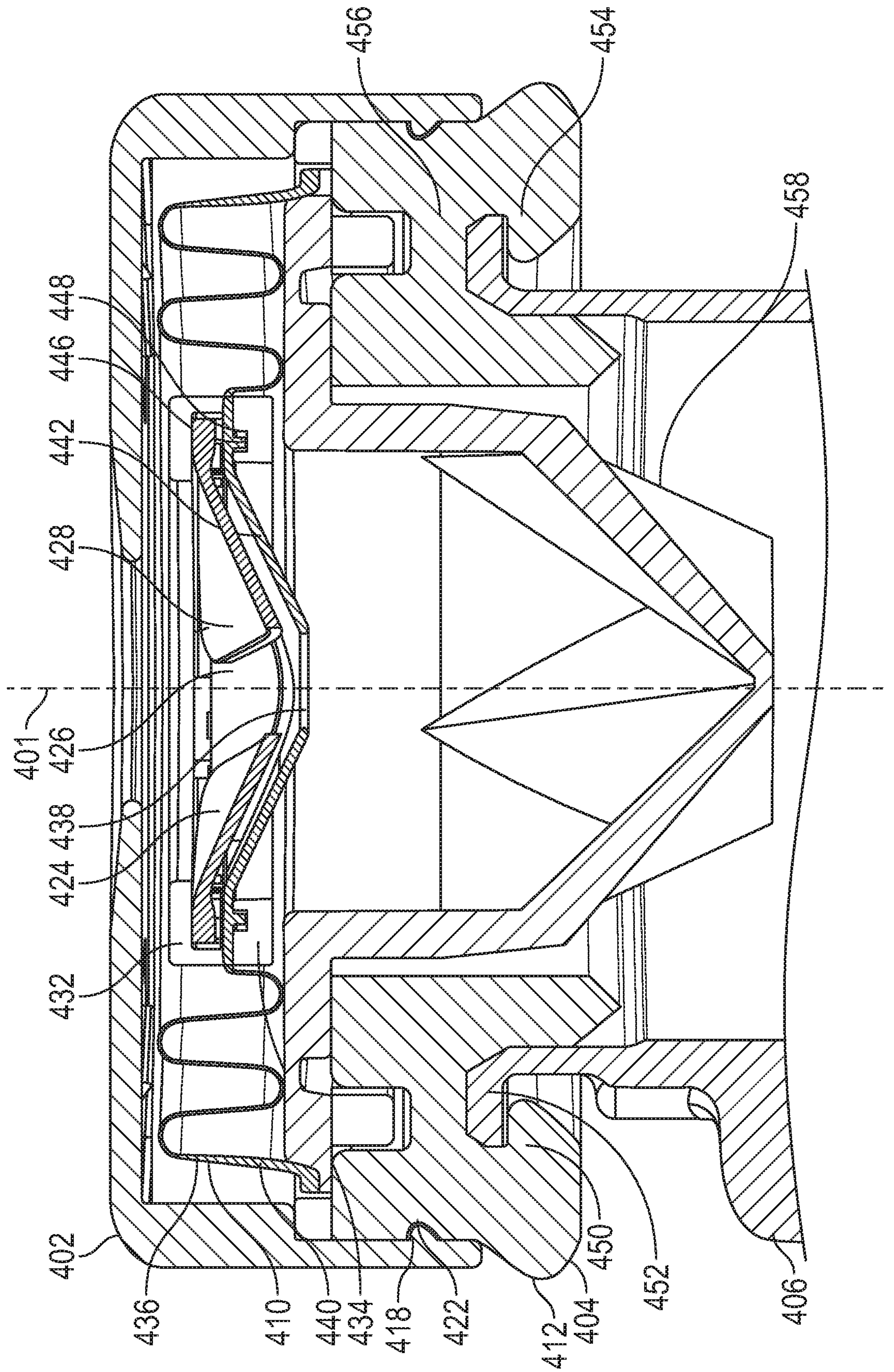
FIG. 4F is a cross-section of the seal shown in FIG. 4A engaged on a cannula.

FIG. 4E is an exploded view of an example bottom portion 404 of the seal 400. FIG. 4F is a cross-section of the assembled seal 400 coupled to the cannula 406. The bottom portion 404 may include a seal portion 410 and a cannula mount 412, which in some examples may be coupled together (e.g., adhered, snapped, screwed, or assembled with connectors) as may be provided as a unitary part, which may be provided in a sterile condition (e.g., sterilized and bagged or packaged.) The cannula mount 412 may be sized and shape to couple (mount) to the an upper portion of the cannula 406. In some examples, the cannula mount may be made of rubber.

The seal portion 410 may include a plurality of flaps 424, 426, 428, a septum seal 440, an upper puck, 432, a lower puck 434 (shown in FIG. 4F), and a slit seal 458. The seal portion 410 may also include protrusions 446 (e.g., annular ring) that may engage an engagement feature 448 (e.g., groove) in the lower puck 434 (e.g., as in the manner described above in reference to the components that form the puck assembly 220) to hold the parts together and avoid slippage of the septum portion 442 relative to the upper and lower puck parts 432, 434 when an instrument is inserted through an opening 438 in the septum portion 442 of the septum seal 440. The bellows 436 may permit the septum portion 442 and upper and lower puck part 432, 434 to move laterally (e.g., perpendicular to the insertion axis 401), which may protect the septum portion of the seal or permit easier movement or greater range of motion for an instrument shaft (not shown in FIG. 4F) inserted through the seal. In some examples, the seal portion 410 may be or include the puck assembly 220 and septum seal 212 described above and shown in FIG. 2A.

The cannula mount 412 may include engagement feature 422, which may be a groove (as shown), or alternatively may be a lip or other structure. The engagement feature 422 may be sized and shaped to engage with the ridges 418 on the inside of the cap 402. The engagement feature 422 may extend all the way around the cannula mount 412 and may be have a consistent height, or the engagement feature 422 may be segmented or tapered, e.g. the engagement feature may be sized and shaped similar to the segmented tapered ridges 418 on the underside of the cap. Squeezing the cap 402 may cause the side portions to move outward as shown in FIG. 4A, causing the ridges 418 to disengage (or lessen their engagement) with the engagement feature 422 and thereby allow the cap 402 to be removed from the seal. Alternatively, the cannula mount 412 may be squeezed inward (toward the insertion axis 401) to move the engagement feature 422 away from the cap 402. In some examples, both squeezing of the cap 402 and inward movement of the cannula mount 412 may be required to release the cap 402 from the bottom portion 404. In some examples, mounting the cannula mount 412 on the cannula 406 may prevent sufficient squeezing of the cannula mount 412 toward the insertion axis, which may prevent removal of the cap 402 from the bottom portion 404 when the seal 400 is mounted to a cannula 406.

As shown in FIG. 4F, the cannula mount 412 may include a cannula engagement feature 450 (e.g., lip and groove), which may be sized and shaped to engage with an engagement feature 452 (e.g., lip) on the cannula 406. In some examples, the engagement feature 450 may be sized and shaped to seal against the cannula 406, which may eliminate a need for an O-ring seal (in contrast to the example shown in FIG. 3E.) For example, a bottom portion 454 of the engagement feature 452 may extend around and below the engagement feature 452 on the cannula to retain the cannula 406 and press the cannula into an upper portion 456 of the engagement feature 452, e.g., so that multiple surfaces of the of the cannula mount 412 are sealed against the cannula 406. The cannula mount 412 may be formed of polyisoprene, or another rubber or a flexible plastic material. Forming the cannula mount 412 of rubber may provide advantageous with respect to sealing against the cannula 406 or for removably coupling with the cap 402.

Figure 5B:
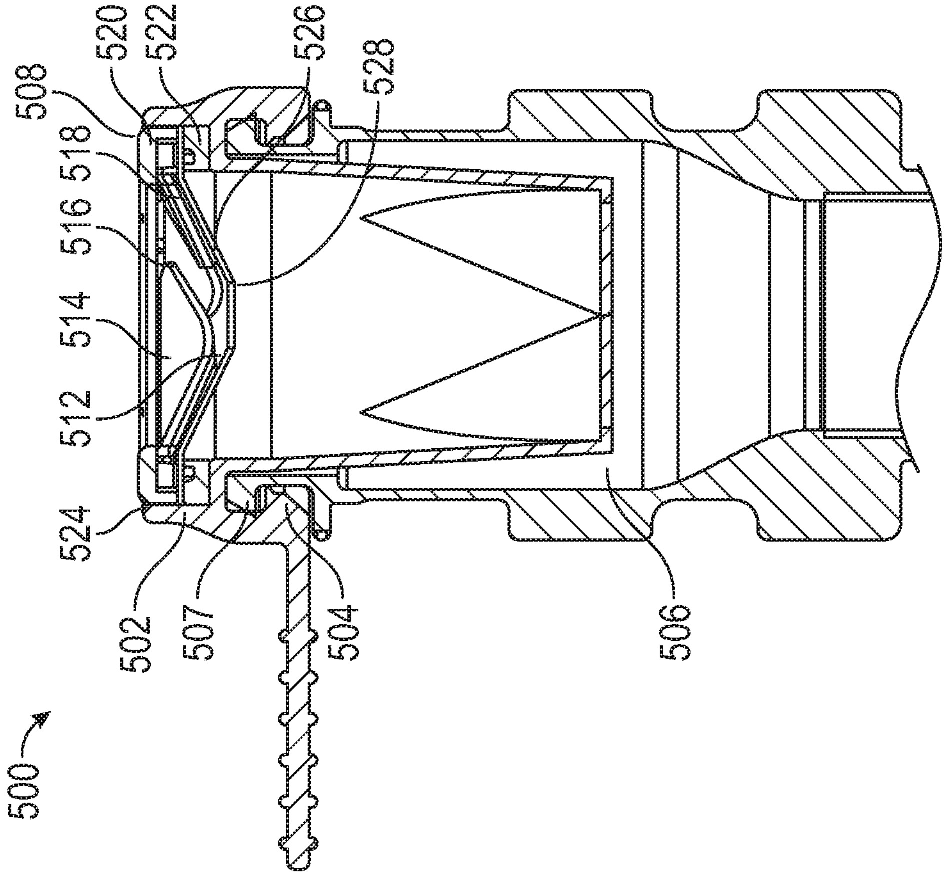
FIG. 5B is a cross-sectional view of the seal and cannula shown in FIG. 5A.
Figure 5A:
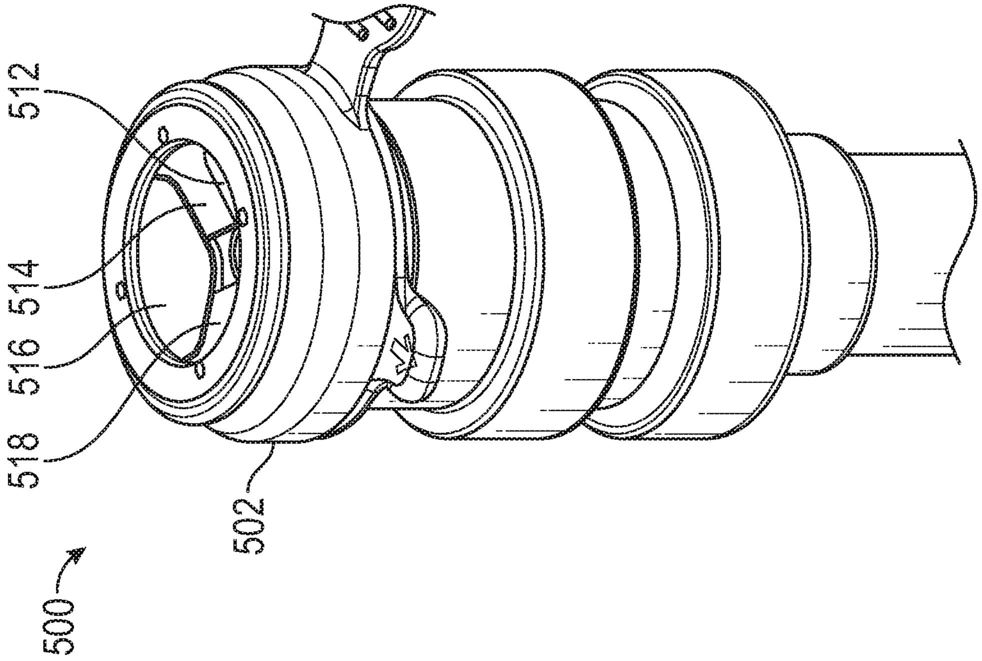
FIG. 5A is a perspective view of an example seal and a cannula.

FIGS. 5A-5B show another example seal 500 that may include a slit seal 502 that includes a cannula engagement feature 504 that is sized and shaped to engage and seal against a cannula 506. In some examples, the engagement feature 504 may wrap around a lip 507 on the cannula 506, similar to the engagement feature 450 described above and shown in FIG. 4F. The slit seal 502 may include a receiving space 524 sized and shaped to receive a puck assembly 508, which may be the puck assembly 220 shown in FIG. 2C and described above. The slit seal 502 may, for example, be formed of polyisoprene or another rubber.

The puck assembly 508 may include a septum seal 526 that may have an opening 528 for sealing against an instrument shaft (not shown in FIG. 5A-5C). The puck assembly may also include a plurality of flaps 512, 514, 516, 518 that may each include a flap portion, flexure portion, and flange portion having an opening as described in reference to the flaps show in FIG. 2D. The puck assembly may also include upper puck part 520 and a lower puck part 522. As described above and shown in FIG. 3D, the lower puck part 522 may include protrusions that extend through openings in the flaps 512, 514, 516, 518 and septum seal 526 and into corresponding receiving portions in the upper puck (or vice-versa, or the protrusions and receiving portions may be mixed between upper and lower pucks.)

In various examples, the slit seal 502 may stretch to receive the puck assembly 508 into the receiving space 524 and the puck assembly 508 may be retained by compression forces exerted by the slit seal 502 (e.g., the puck assembly may be designed to provide an interference fit with the receiving space 524), or a retaining feature (e.g., a lip that engages a groove or another lip) on the slit seal may hold the puck assembly 508 in the receiving space 524, or a cap (not shown in FIGS. 5A-5B, optionally configured as cap 402 in FIG. 4A) may be placed over the puck, or the puck may not be retained (e.g., in a non-pressurized system.) The seal 500 may be desirable due to lower cost or simpler assembly on due to use of fewer parts while still providing desirable sealing and performance characteristics.

Persons of skill in the art will understand that any of the features described above may be combined with any of the other example features, as long as the features are not mutually exclusive. All possible combinations of features are contemplated, depending on clinical or other design requirements. In addition, if manipulating system units are combined into a single system (e.g., telesurgery system), each individual unit may have the same configuration of features, or, one manipulating system may have one configuration of features and another manipulating system may have a second, different configuration of features.

The examples (e.g., methods, systems, or devices) described herein may be applicable to surgical procedures, non-surgical medical procedures, diagnostic procedures, cosmetic procedures, and non-medical procedures or applications. The examples may also be applicable for training, or for obtaining information, such as imaging procedures. The examples may be applicable handling of tissue that has been removed from human or animal anatomies and will not be returned to a human or animal, or for use with human or animal cadavers. The examples may be used for industrial applications, general robotic uses, manipulation of non-tissue work pieces, as part of an artificial intelligence system, or in a transportation system.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) still encompassed by this description. Coordinate systems or reference frames are provided for aiding explanation, and implantations may use other reference frames or coordinate systems other than those described herein.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

We claim:

1. A medical device comprising:

a septum seal including a septum wall, a septum opening defined in the septum wall, and a bellows portion having a plurality of corrugated walls extending around the septum wall;

a plurality of flaps coupled to the septum seal and extending over the septum wall toward the septum opening; and a slit seal aligned with and distal to the septum seal, wherein the plurality of flaps are arranged to define a flap opening proximal to and aligned with the septum opening, wherein the slit seal includes a seal portion and a rim portion, wherein each of the plurality of corrugated walls includes a proximally-distally extending portion and a laterally extending portion, wherein the laterally extending portions of the plurality of corrugated walls are concentric with one another and the septum wall and are arranged at positions successively radially outward of the septum wall, and wherein the slit seal directly contacts and seals against one or more of the laterally extending portions of the plurality of corrugated walls of the bellows portion of the septum seal.

2. The medical device of claim 1, wherein:

the medical device further comprises a puck structure; and the plurality of flaps and the septum seal are coupled to the puck structure.

3. The medical device of claim 2, wherein:

the medical device further comprises a housing;

the housing includes an upper housing part and a lower housing part removably coupled to the upper housing part; and the septum seal, the slit seal, the plurality of flaps, and the puck structure are between the upper housing part and the lower housing part.

4. The medical device of claim 3, wherein:

the medical device further comprises a cap between the bellows portion and the upper housing part; and the cap inhibits inflation of the bellows portion in response to a pressure change distal to the bellows portion.

5. The medical device of claim 4, wherein:

the upper housing part includes a guide portion sized and shaped to guide an instrument toward the septum opening; and the guide portion extends past the cap.

6. The medical device of claim 3, wherein:

the upper housing part is in the shape of an oval; and the upper housing part is configured to be squeezed on an elongated portion of the shape of the oval to release the upper housing part from the lower housing part.

7. The medical device of claim 2, wherein:

the septum seal includes a second opening; and the puck structure includes a first puck part, a second puck part, and a protrusion that extends through the second opening to couple the first puck part and the second puck part to one another and to the septum seal and the plurality of flaps.

8. The medical device of claim 7, wherein:

the septum seal includes a rim portion surrounding the septum wall;

the bellows portion surrounds the rim portion; and the second opening is in the rim portion of the septum seal.

9. The medical device of claim 8, wherein:

the puck structure is sized and shaped to fit the rim portion of the septum seal.

10. The medical device of claim 7, wherein:

the septum seal includes a reinforcement structure around the second opening.

11. The medical device of claim 2, wherein:

the puck structure includes a lubrication channel extending from a top surface of the puck structure to a space between the plurality of flaps and the septum wall.

12. The medical device of claim 11, wherein:

the puck structure includes a proximal puck part and a distal puck part; and the lubrication channel includes a proximal opening in a proximal surface of the proximal puck part, a distal opening adjacent the space between the plurality of flaps and the septum wall, and a passageway in the proximal puck part connecting the proximal opening and the distal opening.

13. The medical device of claim 2, wherein:

the bellows portion flexes as the puck structure, the plurality of flaps, and the septum opening move to accommodate movement of an instrument inserted through the flap opening and the septum opening.

14. The medical device of claim 2, wherein:

the septum seal includes a retaining structure that engages the puck structure and restrains movement of the septum wall with respect to the puck structure.

15. The medical device of claim 1, wherein:

the flap opening is in the shape of a polygon.

16. The medical device of claim 1, wherein:

each of the plurality of flaps includes a flange portion connected to a flap portion by a flexure portion;

the flange portion is coupled to the septum seal; and the flexure portion is configured to flex distally on a condition that an instrument is inserted through the flap opening.

17. The medical device of claim 16, wherein:

the flap portion includes first and second side portions and a center portion; and the first and second side portions are curved proximally relative to the center portion.

18. A medical device comprising:

a septum seal including a septum wall, a septum opening defined in the septum wall, and a bellows portion extending around the septum wall;

a plurality of flaps coupled to the septum seal and extending over the septum wall toward the septum opening; and a slit seal aligned with and distal to the septum seal; and a puck structure, wherein:

the plurality of flaps are arranged to define a flap opening proximal to and aligned with the septum opening, the slit seal includes a seal portion and a rim portion;

the slit seal directly contacts and seals against the bellows portion of the septum seal;

the plurality of flaps and the septum seal are coupled to the puck structure;

the septum seal includes a second opening; and the puck structure includes a first puck part, a second puck part, and a protrusion that extends through the second opening to couple the first puck part and the second puck part to one another and to the septum seal and the plurality of flaps.

* * * * *